(12) United States Patent
Shukla et al.

(10) Patent No.: US 8,404,892 B2
(45) Date of Patent: Mar. 26, 2013

(54) AROMATIC AMIC ACID SALTS AND COMPOSITIONS

(75) Inventors: Deepak Shukla, Webster, NY (US); Dianne M. Meyer, Hilton, NY (US); Wendy G. Ahearn, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 174 days.

(21) Appl. No.: 12/788,347

(22) Filed: May 27, 2010

(65) Prior Publication Data

US 2011/0295010 A1  Dec. 1, 2011

(51) Int. Cl.
*C07C 233/00* (2006.01)
*C07C 235/02* (2006.01)
(52) U.S. Cl. ..................................................... 564/156
(58) Field of Classification Search .................. None
See application file for complete search history.

(56) References Cited

U.S. PATENT DOCUMENTS

| 4,496,731 | A  | * | 1/1985  | Spietschka et al. ............. 546/37 |
|-----------|----|---|---------|---------------------------------------|
| 5,650,513 | A  |   | 7/1997  | Langhals et al.                       |
| 6,387,727 | B1 |   | 5/2002  | Katz et al.                           |
| 7,422,777 | B2 |   | 9/2008  | Shukla et al.                         |
| 7,579,619 | B2 |   | 8/2009  | Shukla et al.                         |
| 2002/0164835 | A1 |   | 11/2002 | Dimitrakopoulos et al.             |
| 2005/0176970 | A1 |   | 8/2005  | Marks et al.                        |
| 2008/0135833 | A1 |   | 6/2008  | Shukla et al.                       |
| 2009/0256137 | A1 |   | 10/2009 | Shukla et al.                       |
| 2011/0137137 | A1 | * | 6/2011  | Shin et al. ..................... 600/301 |
| 2011/0266523 | A1 | * | 11/2011 | Shukla et al. ................... 257/40 |
| 2011/0269265 | A1 | * | 11/2011 | Shukla et al. ................... 438/99 |
| 2011/0269967 | A1 | * | 11/2011 | Shukla et al. ................. 546/110 |

FOREIGN PATENT DOCUMENTS

| EP | 0 805 154 | 11/1997 |
|----|-----------|---------|
| WO | 92/00283  | 1/1992  |
| WO | 95/04305  | 2/1995  |

OTHER PUBLICATIONS

Liu Zhongyuan et al: "Highly Sensitive Reagentless Amperometric Immunosensor Based on Layer-By-Layer Assembly of Redox-Active Organic-Inorganic Composite Film for Determining Prostate Specific Antigen", Huaxue Xuebao, Kexue Chubanshe, CN, vol. 67, No. 7, Jan. 1, 2009, pp. 637-644, XP008140251, ISSN: 0567-7351, PCT-NH2.
Kheifets G M et al: "Hydrolysis of N,N'-disubstituted diimides of 1,4,5,8-naphthalenetetracarboxylic acid. I. Structure of Hydrolysis Products and Equilibrium Position in Relation to the pH of the Medium", Zhurnal Organicheskoi Khimii, Maik Nauka, Moscow, RU, vol. 18, No. 8, Jan. 1, 1982, pp. 1750-1759, XP008140252, ISSN: 0514-7492, Compounds IIIa-e.
Kim et al.: J. Phys. Org. Chem., vol. 21, 2008, pp. 731-737, XP002650877, cited in the application, figure 5.
Ponce P. et al: "Bisimide-Lactamimide Ring Contraction in Six-Membered Bisimides: A Theoretical Study", Journal of Physical Organic Chemistry, Wiley, GB, vol. 14, Jan. 1, 2001, pp. 657-666, XP008042431, ISSN: 0894-3230, DOI: DOI: 10.1002/POC.409, Figure 1.
Feiler, L. et al.: Liebigs Ann., 1995, pp. 1229-1244, XP002655595, Figure 3.
U.S. Appl. No. 12/770,803, filed Apr. 30, 2010, titled Aromatic Amic Acids or Amic Esters and Compositions, by D. Shukla et al.
U.S. Appl. No. 12/788,349, filed May 27, 2010, titled Methods of Providing Semiconductor Layers From Amic Acid Salts by D. Shukla et al.
U.S. Appl. No. 12/788,355, filed May 27, 2010, titled Articles Containing Coatings of Amic Acid Salts, by D. Shukla et al.
John A. Kreuz et al, "Studies of Thermal Cyclizations of Polyamic Acids and Tertiary Amine Salts", J. of Polymer Sci.: Part A-1, vol. 4, 2607-2616 (1966).
C. Genies et al, "Soluble sulfonated naphthalenic polyimides as materials for proton exchange membranes",Elsevier Sci. Ltd., *Polymer* 42 (2001) 359-373.
S.I. Kim et al, "Glass transition behaviours in aromatic poly(amic dialkyl ester) precursors with various chain rigidities" Elsevier Sci Ltd., *Polymer* 40 (1999) 2263-2270.
J.V. Facinelli et al, "Controlled Molecular Weight Polyimides from Poly(amic acid) Salt Precursors", *Macromolecules* 1996, 29, 7342-7350, Am Chem Soc.
Yong Ding et al, "Polyimide Membranes Derived from Poly(amic acid) Salt precursor Polymers. 1.1 Synthesis and Characterization" *Macromolecules* 2002, 35, 905-911, Am Chem Soc.
Bubin Xu et al, "Polyimides from diamine-acid salts and tetracarboxylic dianhydrides",*Macromol. Rapid Commun.* 21, No. 8, 481-484 (2000).
Jun Yang et al, "A Water-Soluble Polyimide Precursor: Synthesis and Characterization of Poly(amic acid) Salt", *Macromolecular Research*, vol. 12, No. 3, pp. 263-268 (2004).
Michelle B. Kim et al, "Hydrolysis of aliphatic naphthalene diimides: effect of charge placement in the side chains", *J. Phys. Org. Chem.* 2008, 21, 731-737.

* cited by examiner

*Primary Examiner* — Kamal Saeed
*Assistant Examiner* — Nyeemah A Grazier
(74) *Attorney, Agent, or Firm* — J. Lanny Tucker

(57) ABSTRACT

Aromatic non-polymeric amic acid salts are designed to be thermally converted into corresponding arylene diimides. These aromatic, non-polymeric amic acid salts can be used to prepare semiconducting thin films that can be used in various articles including thin-film transistor devices that can be incorporated into a variety of electronic devices. In this manner, the arylene diimide need not be coated but is generated in situ from a solvent-soluble, easily coated aromatic, non-polymeric amic acid salt at relatively lower temperature because the cation portion of the amic acid salt acts as an internal catalyst.

8 Claims, 4 Drawing Sheets

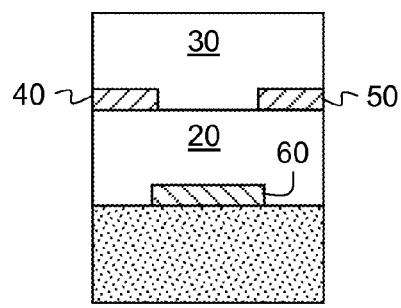
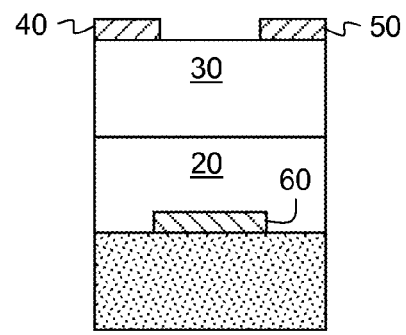
FIG. 1a　　　　　　　　FIG. 1b
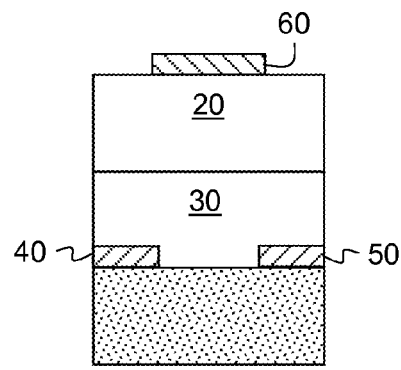
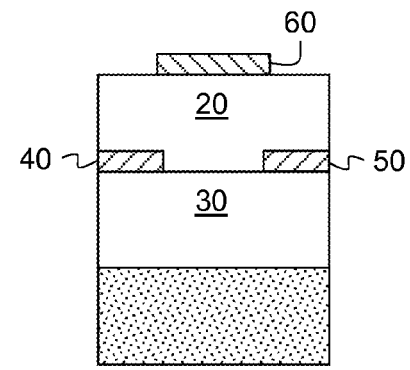
FIG. 1c　　　　　　　　FIG. 1d

AROMATIC AMIC ACID SALTS AND COMPOSITIONS

FIELD OF THE INVENTION

This invention relates to a unique class of aromatic non-polymeric amic acid salts that can be provided as compounds or compositions and that are capable of being thermally converted into corresponding arylene diimides at lower temperatures as the salt cation acts as an internal catalyst for thermal conversion.

BACKGROUND OF THE INVENTION

Considerable efforts have been made to discover new organic semiconductor materials that can be used in FET's to provide switching or logic elements in electronic components, many of which require significant mobilities well above 0.01 $cm^2$/V.sec, and current on/off ratios (hereinafter referred to as "on/off ratios") greater than 1000. Organic FET's ("OFET's") having such properties can be used for electronic applications such as pixel drivers for displays and identification tags. However, most of the compounds exhibiting these desirable properties are "p-type" or "p-channel," meaning that negative gate voltages, relative to the source voltage, are applied to induce positive charges (holes) in the channel region of the device.

As an alternative to p-type organic semiconductor materials, n-type organic semiconductor materials can be used in FET's where the terminology "n-type" or "n-channel" indicates that positive gate voltages, relative to the source voltage, are applied to induce negative charges in the channel region of the device.

Moreover, one important type of FET circuit, known as a complementary circuit, requires an n-type semiconductor material in addition to a p-type semiconductor material. Simple components such as inverters have been realized using complementary circuit architecture. Advantages of complementary circuits, relative to ordinary FET circuits, include lower power dissipation, longer lifetime, and better tolerance of noise. In such complementary circuits, it is often desirable to have the mobility and the on/off ratio of an n-channel device similar in magnitude to the mobility and the on/off ratio of a p-channel device. Hybrid complementary circuits using an organic p-type semiconductor and an inorganic n-type semiconductor are known, but for ease of fabrication, an organic n-channel semiconductor material would be desired in such circuits.

Only a limited number of organic materials have been developed for use as a semiconductor n-channel in OFET's. One such material, buckminsterfullerene $C_{60}$, exhibits a mobility of 0.08 $cm^2$/V.sec but it is considered unstable in air (Haddon et al. *Appl. Phys. Let.* 1995, 67, 121). Perfluorinated copper phthalocyanine has a mobility of 0.03 $cm^2$/V.sec and is generally stable to air operation, but substrates must be heated to temperatures above 100° C. in order to maximize the mobility in this material (Bao et al. *Am. Chem., Soc.* 1998, 120, 207). Other n-channel semiconductors, including some based on a naphthalene framework, have also been reported, but with lower mobilities. One such naphthalene-based n-channel semiconductor material, tetracyanonaphthoquinodimethane (TCNNQD), is capable of operation in air, but the material has displayed a low on/off ratio and is also difficult to prepare and purify.

Aromatic tetracarboxylic diimides, based on a naphthalene aromatic framework, have also been demonstrated to provide, as an n-type semiconductor. Thus, in naphthalene diimide-based OFET's, U.S. Pat. No. 6,387,727 (Katz et al.) teaches n-channel mobilities up to 0.16 $cm^2$/V.sec. Comparable results were obtained with bottom contact devices, but a thiol underlayer had to be applied between the gold electrodes and the semiconductor as described. In the absence of the thiol underlayer, the mobility of the naphthalene diimide derivatives in U.S. Pat. No. 6,387,727 was found to be orders of magnitude lower in bottom-contact devices. This patent also discloses fused-ring tetracarboxylic diimide compounds, one example of which is N,N'-bis(4-trifluoromethyl benzyl)naphthalene diimide. The highest mobilities of 0.1 to 0.2 $cm^2$/V.sec were reported for N,N'-dioctyl naphthalene diimide.

In a different study, using pulse-radiolysis time-resolved microwave conductivity measurements, relatively high mobilities have been measured in films of naphthalene diimides having linear alkyl side chains (Struijk et al., *J. Am. Chem. Soc. Vol.* 2000, 122, 11057).

U.S. Patent Application Publication 2002/0164835 (Dimitrakopoulos et al.) discloses n-channel semiconductor films made from perylene diimide compounds, as compared to naphthalene-based compounds, one example of which is N,N'-di(n-1H,1H-perfluorooctyl)perylene diimide. Substituents attached to the imide nitrogens in the diimide structure comprise alkyl chains, electron deficient alkyl groups, and electron deficient benzyl groups, and the chains preferably having a length of four to eighteen atoms. Devices based on materials having a perylene framework used as the organic semiconductor have low mobilities, for example $10^{-5}$ $cm^2$/V.sec for perylene tetracarboxylic dianhydride (PTCDA) and $1.5 \times 10^{-5}$ $cm^2$/V.sec for N,N'-diphenyl perylene diimide (PTCDI-Ph) (Horowitz et al. *Adv. Mater.* 1996, 8, 242 and Ostrick et al. *J. Appl. Phys.* 1997, 81, 6804).

In perylene and naphthalene diimide based OFET's, many experimental studies have demonstrated that morphology of the thin film has strong impact on the device performances. Theoretical calculation and experimental characterization (particularly X-ray diffraction), have shown that the molecular packing in PDI is very sensitive to the side chains (Kazmaier et al. *J. Am. Chem. Soc.* 1994, 116, 9684). In perylene diimide based n-channel OFET devices, changing the side chain from n-pentyl to n-octyl increases the field effect mobility of from 0.055 $cm^2$/V.sec to 1.3 $cm^2$/V.sec, respectively (Chesterfield et al. *J. Phys. Chem. B* 2004, 108, 19281). Such sensitivity to the type of side-chain is a manifestation of an aggregation effect and it provides potentially an effective way to control and optimize the molecular packing for enhanced $\pi$-orbital overlap between neighboring molecules, a necessary for efficient carrier transport. U.S. Pat. No. 7,422,777 (Shukla et al.) discloses N,N'-dicycloalkyl-substituted naphthalene diimide compounds, which in thin films, exhibit optimum packing and exhibit n-channel mobility up to 6 $cm^2$/V.sec in OFET's. U.S. Pat. No. 7,579,619 (Shukla et al.) discloses N,N'-di(arylalkyl) substituted naphthalene diimide compounds that exhibit high n-channel mobility up to 3 $cm^2$/V.sec in top-contact OFET's.

A variety of naphthalene diimides have been made and tested for n-type semiconducting properties. In general, these materials, as an n-type semiconductor, have provided n-channel mobilities up to 6 $cm^2$/V.sec using top-contact configured devices. However, besides charge mobility, improved stability and integrity of the semiconductor layer are important goals.

U.S. Patent Application Publication 2005/0176970 (Marks et al.) discloses improved n-channel semiconductor films made of mono- and diimide perylene and naphthalene compounds wherein the nitrogen and core are substituted with electron withdrawing groups. Substituents attached to the imide nitrogen's in the diimide structure can be selected from alkyl, cycloalkyl, substituted cycloalkyl, aryl, and substituted aryl groups. However, this publication fails to suggest any comparative advantage of using cycloalkyl groups on the imide nitrogen atoms. Accordingly, mobilities obtained from perylene diimides containing of N-octyl and N-cyclohexyl are virtually indistinguishable (see Example 10 of the publication). Furthermore, the highest mobilities reported in this reference are 0.2 $cm^2$/V.sec and the reference fails to show experimental data with respect to naphthalene compounds and require that their core be cyano di-substituted.

Aromatic tetracarboxylic diimides, based on a naphthalene and perylene aromatic framework have been widely used as n-type semiconductor materials (Newman et al. *Chem. Mater.* 2004, 16, 4436-4451). Relatively low mobilities have been measured in films of naphthalene tetracarboxylic diimides having linear alkyl side chains using pulse-radiolysis time-resolved microwave conductivity measurements. See Struijk et al. "Liquid Crystalline Perylene Diimides: Architecture and Charge Carrier Mobilities" *J. Am. Chem. Soc. Vol.* 2000, 122, 11057. However, TFT's based on N,N'-dicyclo-substituted naphthalene diimide exhibit mobility up to 5 $cm^2$/V.sec (Shukla et al. *Chem. Mater.* 2008, 20, 7486-7491). U.S. Pat. No. 6,387,727 (Katz et al.) discloses fused-ring tetracarboxylic diimide compounds, such as N,N'-bis(4-trifluoromethyl benzyl)naphthalene-1,4,5,8,-tetracarboxylic acid diimide. The highest mobilities reported in this patent is between 0.1 and 0.2 $cm^2$/V.sec for N,N'-dioctyl naphthalene-1,4,5,8-tetracarboxylic acid diimide.

It is widely recognized that the morphology and microstructure of an organic thin film has a strong impact on the charge carrier mobility and OTFT device characteristics. In general, organic materials that form highly oriented polycrystalline thin films exhibit high charge carrier mobility. At the molecular level, it is the basic chemical structure of the molecule that controls intermolecular interactions that determines if a material will be crystalline or amorphous. The extent of π-stacking between the molecules determines whether the organic film will be highly crystalline or totally amorphous. Thus, to have well-defined thin film morphology, it is necessary to control materials on the molecular scale. This necessitates adapting the basic structure of semiconducting molecules in a way that results in an optimum crystalline packing arrangement.

It is known that diimide based semiconductors are very sensitive to the substitutions on the nitrogen atoms of the diimide rings. Such sensitivity to the side-chain is a manifestation of subtle changes in diimide aggregation in solid state and provides potentially an effective way to control and optimize the molecular packing for enhanced π-orbital overlap between neighboring molecules, a necessity for efficient carrier transport. Accordingly, U.S. Pat. No. 7,422,777 (Shukla et al.) discloses N,N'-dicycloalkyl-substituted naphthalene diimide compounds, which in thin films, exhibit optimum packing and exhibit n-channel mobility up to 6 $cm^2$/V.sec in OFET's. In another example, U.S. Pat. No. 7,579,619 (Shukla et al.) discloses N,N'-di(arylalkyl) substituted naphthalene diimide compounds that exhibit high n-channel mobility up to 3 $cm^2$/V.sec in top-contact OFET's. These materials consistently exhibit higher mobility compared to a naphthalene tetracarboxylic diimide having phenyl substituents.

U.S. Patent Application Publications 2008/0135833 (Shukla et al.) and 2009/0256137 (Shukla et al.) describe n-type semiconductor materials for thin film transistors that include configurationally controlled N,N'-dicycloalkyl-substituted naphthalene 1,4,5,8-bis-carboximide compounds or N,N'-1,4,5,8-naphthalenetetracarboxylic acid imides having a fluorinated substituent, respectively. In these cycloalkyl-substituted naphthalene diimide derivatives, the effect of the alkyl group configuration in the cycloalkyl ring affects the aggregation, and hence the carrier mobility, in solid state.

Recently, dicyanated arylene diimide semiconductors based on perylene and naphthalene diimide cores have been developed that are solution processable and show environmental stability (*Adv. Funct. Mater.* 2008, 18, 1329-1339). The latter characteristics arise from cyano group addition to the core, which increases solubility by decreasing molecular planarity and stabilizes charge carriers by lowering the energies of the lowest unoccupied molecular orbital's associated with electron transport. While high temperature vapor deposited devices using these materials show good mobilities (ca. 0.1-0.5 $cm^2$/V.sec; Jones et al. *Adv. Funct. Mater.* 2008, 18, 1329-1339), solution coated device usually give lower mobility and exhibit low $I_{on}/I_{off}$ ratio.

As is clear from the foregoing discussion, the development of new semiconducting materials, both p-type and n-type, continues to be an enormous topic of interest and unpredictable as to the semiconductive properties of various compounds. Among n-type diimide based materials, the highest charge carrier mobility (ca. 5.0 $cm^2$/V.sec) in thin film transistors has been observed with N,N'-dicyclohexyl naphthalene diimide. However, the poor solubility of this material limits its practical application potential. Although, as discussed above, dicyanated arylene diimide semiconductors based on perylene and naphthalene diimide cores are solution processable and show environmental stability their carrier mobility is low. To attain solubility extensive molecular modification have to be made which usually lowers the crystallinity of the material (for example see et al. *Adv. Funct. Mater.* 2008, 18, 1329-1339) that usually results in lower mobility in OTFT devices.

Efforts continue to improve performance of n-type organic semiconductor materials in OTFT's and technology for their manufacture and use. Specifically there continues to be research efforts to find new materials and processes that are useful in n-type semiconducting materials which compounds do not require significant structural modification to achieve processability and optimum crystalline packing.

Amic acids are usually more soluble than aromatic anhydrides they are derived from. One attractive way of obtaining solution-processed thin films of diimide based semiconductors is to solution coat an amic acid and then by thermal dehydration reaction, convert it to the corresponding diimide.

The dehydration of amic acids, derived from the reaction of cyclic anhydrides with primary amines, to yield imides is a general method for the preparation of this important class of heterocyclic compounds and is of major commercial significance in the conversion of polyamic acids to polyimides (Kreuz, Endrey, Gay, and Sroog, *J. Polym. Sci., Part A,* 4, 2607 (1966), and references contained therein.). As polyimides derived from phthalamic acids possess many desirable attributes, this class have materials have found applications in many technologies ranging from dielectrics in microelectronics to high temperature adhesives to membranes (for example see Mittal, *Polyimides and Other High Temperature Polymers: Synthesis, Characterization and Applications* vol. 1 to 5). Most of the detailed studies have concentrated on preparation of polyphthalamic acids and their conversion to polyimides in solid films (for example, see Kim et al. in Polymer 40, 1999, pp 2263-2270, and references cited therein). In contrast, little is known about the dehydration reactions of amic acids derived from anthracene, naphthalene, and perylene anhydrides or anthracene, naphthalene, and perylene tetracarboxylic acid dianhydrides. Fabienne et al have recently reported mechanistic studies of polycondensation reactions of naphthalene anhydride leading to naphthalimide polymers (Piroux, Mercier, and Picq, *High Performance Polymers* (2009), 21(5), 624-632).

Genies et al. have reported synthesis of soluble sulfonated naphthalenic polyimides, derived from naphthalene dianhydride, as materials for proton exchange membranes (Genies et al. *Polymer* 42 (2001) 359-373).

Copending and commonly assigned U.S. Ser. No. 12/770,803 (filed Apr. 30, 2010 by Shukla, Meyer, and Ahearn) describes novel aromatic amic acids and amic esters that can be thermally converted to corresponding arylene diimides that are formed into semiconductive layers for various articles and devices. These compounds are advantageous in that the semiconductive layers can be formed in situ while the precursor compounds are readily coated from organic solvents.

Salts of poly(amic acids) have also been shown to undergo thermal imidization reaction to generate polyimides. Facinelli et al. have prepared thermoplastic polyimides via poly(amic acid) salt precursors (see Facinelli et al. *Macromolecules* 1996, 29, 7342-7350). These poly(amic acid) salts were prepared in heterogeneous reactions of the poly(amic acid)s using quaternary ammonium bases or triethylamine dissolved in methanol or water to yield soluble salts which were then melt imidized in air at 250° C. or 300° C. for 30 minutes. Ding et al. have prepared polyimide based membranes from poly(amic acid) salts (see Ding et al. *Macromolecules* 2002, 35, 905-911). This publication shows that poly(amic acid) tertiary amine salts can be quantitatively imidized at a lower temperature than the poly(amic acid) or poly(amic acid) quaternary amine salts of identical backbone structure. Xu et al. have synthesized polyimides from a diamine-acid salt and a dianhydride in the presence of excess triethylamine, thereby avoiding the use of air-sensitive aromatic diamine compounds as monomers (Xu et al., *Macromol. Rapid Commun.* 2000, 21, 481-484). Yang et al. have also prepared and characterized poly(amic acid) salts of pyromellitic dianhydride (Yang et al. *Macromolecular Research*, 2004, Vol. 12, No. 3, pp 263-268). Polyimide multilayer thin films prepared from poly(amic acid) and poly(amic acid) ammonium salt are described in *Macromolecular Research,* 2008, Vol. 16, No. 8, pp 725-733. WO 95/04305 (Flattery et al.) discloses a photosensitive composition of a fluorinated poly(amic acid) aminoacrylate salt.

WO 92/00283 (Goze et al.) discloses the use of N,N'-disubstituted amic acid ammonium salts, their use as surfactants, emulsifiers, suspending agents, and conditioning agents in shampoos. This publication does not teach thermal imidization reaction of such salts. It also fails to disclose amic acids salts of naphthalene or perylene tetracarboxylic acids.

Kim et al. *J. Phys. Org. Chem.* 2008, 21 731-737 describes the formation of amic acid salts in the hydrolysis of certain aliphatic naphthalene diimides. However, the publication does not isolate these salts or teach their thermal imidization reaction. EP 0 805 154A1 (Iwasawa et al.) discloses certain N,N-disubstituted amic acid derivatives as in-vivo inhibitors of protein-farnesyl transferase (PFT).

The use of such amic acid and amic ester precursor compounds have a number of advantages, as described in the U.S. Ser. No. 12/770,803 described above, but there is a need to provide semiconductive layers at lower temperatures, or even at room temperature, to improve manufacturing processes.

SUMMARY OF THE INVENTION

This invention provides an organic composition that comprises new aromatic, non-polymeric amic acid salts. Such compositions can consist only of the aromatic non-polymeric amic acid salts, or such compounds can be provided in solution form with one or more solvents.

In many useful embodiments, the aromatic, non-polymeric amic acid salts of this invention are represented by any of Structures (I), (II), (Ia), (Ib), (IIa), and (IIb) that are defined below.

The aromatic, non-polymeric compounds of this invention can be used to prepare thin films that are thermally convertible to corresponding semiconductive arylene diimide compounds, such as, naphthalene diimides. Thus, the arylene diimides are obtained via solid state thermal dehydration imidization reaction of the organic-soluble precursor aromatic, non-polymeric amic acid salts. The aromatic, non-polymeric amic acid salts can be easily prepared in environmentally friendly solvents like methanol, ethanol, or mixtures thereof.

The advantages of this invention are achieved by preparing thin films of semiconducting arylene diimides by solid state thermal dehydration imidization reaction of an aromatic, non-polymeric amic acid salt or mixture of such salts. The presence of the cation in the salt enables lower temperature conversion to the arylene diimides. In other words, the cation appears to act as a catalyst in the thermal conversion reaction. The low temperature processing combined with readily available materials and ease of deposition of thin films over large areas due to solubility of the aromatic, non-polymeric amic acid salts provide an inexpensive and more convenient approach to the fabrication of thin film transistor devices and other semiconductive articles. Furthermore, since, compared to corresponding diimides, aromatic, non-polymeric amic acid salts are readily soluble in a variety of solvents and water, they can be coated on a variety of substrates without additional preparations (such as applying an extra adhesion promotion layer onto the substrate or modifying the substrate surface in some other manner).

The present invention and its advantages will become more apparent when taken in conjunction with the following description, drawings, and the illustrative working examples provided below.

BRIEF DESCRIPTION OF THE DRAWINGS

FIGS. 1a through 1d illustrate cross-sectional views of four possible configurations for an organic field effect transistor. FIGS. 1a and 1b have a bottom gate configuration and FIGS. 1c and 1d have a top gate configuration.

DETAILED DESCRIPTION OF THE INVENTION

Definitions

Figure 2A:
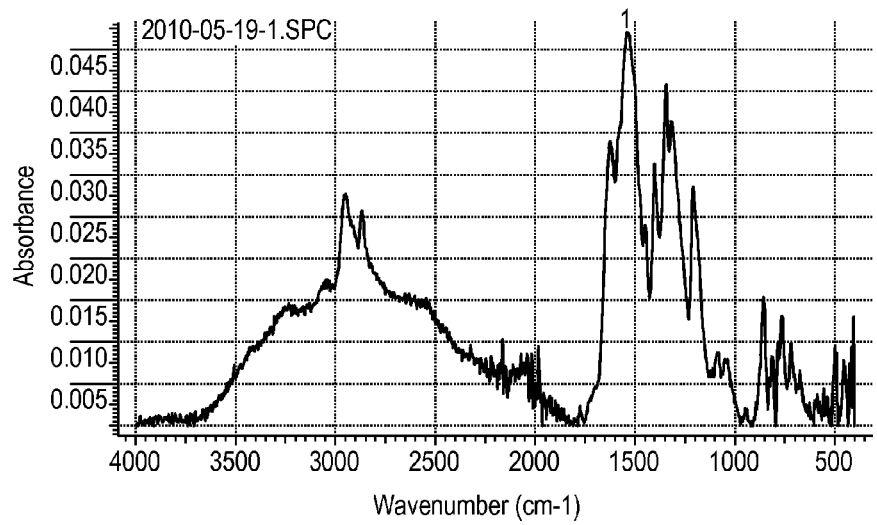
FIGS. 2a, 2b, and 3 are graphical plots of synthetic data obtained in Invention Example 2 below.

As used herein, "a" or "an" or "the" are used interchangeably with "at least one," to mean "one or more" of the components or elements being defined. For example, mixtures of aromatic, non-polymeric amic acid salts can be used to provide mixtures of arylene diimide compounds in the semiconductive layers or coatings. In addition, "solvent" can include mixtures of solvents in which the amic acid salts are dissolved or dispersed.

The aromatic non-polymeric amic acid salts of this invention are "bis" compounds. By "non-polymeric" in reference to the aromatic, non-polymeric amic acid salts of this invention, we mean that the compounds do not contain two or more recurring "bis" units in a chain.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituents unsubstituted form, but also its form to the extent it can be further substituted (up to the maximum possible number) with any other mentioned substituent group or groups (mentioned for the same position) so long as the substituent does not destroy properties necessary for semiconductor utility. If desired, the substituents can themselves be further substituted one or more times with acceptable substituent groups. When a molecule can have two or more substituents, the substituents can be joined together to form an aliphatic or unsaturated ring unless otherwise provided.

Aromatic, Non-Polymeric Amic Acid Salts and Compositions n-Channel organic semiconductor layers (or thin films) can include one or more of arylene diimide compounds. This layer is capable of exhibiting a field effect electron mobility that is greater than 0.0001 $cm^2$/V.sec, or greater than 0.1 $cm^2$/V.sec, or more likely greater than 1 $cm^2$/V.sec. In many useful embodiments, the thin organic semiconductor films (and the devices containing the films) exhibit a field effect electron mobility that is greater than 0.01 $cm^2$/V.sec.

In addition, the n-channel organic semiconductor film is capable of providing on/off ratios of a source/drain current of at least $10^3$ or typically of at least $10^5$. The on/off ratio is measured as the maximum/minimum of the drain current as the gate voltage is swept from zero to 100 volts and the drain-source voltage is held at a constant value of 100 volts, and employing a gate dielectric.

Moreover, these properties are attainable after repeated exposure of the n-type organic semiconducting layer to air before layer deposition as well as exposure of the thin film transistor device or the channel layer to air after layer deposition.

Without wishing to be bound by theory, there are several factors that are believed to contribute to the desirable properties of the organic semiconductor layer containing arylene diimides compounds. The solid-state structure of the arylene diimide compounds described herein exhibit good order in the layer. The molecules are packed such that the orbital's of the conjugated arylene core system containing the arylene ring system or the imide carboxyl groups are able to interact with adjacent molecules, resulting in high mobility. The direction of this interaction has a component parallel to the direction of desired current flow in a device using this material in the semiconductor layer. The morphology of the layer formed by arylene diimides is substantially continuous such that current flows through the material without unacceptable interruption. However, it is particularly advantageous that the arylene diimide layer is not only continuous but also exhibits polycrystalline morphology with minimum inter-grain defects so that current flows through the material without unacceptable interruption. The stereochemistry of the substituent on the arylene diimides is such that they do not disrupt the intrinsic ability of these molecules to pack in an effective crystalline arrangement.

The lowest lying unoccupied molecular orbital of the arylene diimide compound is at an energy that allows for injection of electrons in the compound at useful voltages from metals with reasonable work functions. Arylene diimides (such as naphthalene diimides and perylene diimides) described herein have a desirable lowest unoccupied molecular orbital (LUMO) energy level of about 3.0 eV to about 4.6 eV with reference to the vacuum energy level. As known in the art, LUMO energy level and reduction potential approximately describe the same characteristics of a material. LUMO energy level values are measured with reference to the vacuum energy level, and reduction potential values are measured in solution versus a standard electrode. An advantage for thin film transistor devices is that the LUMO in the crystalline solid, which is the conduction band of the organic semiconductor, and the electron affinity of the solid both are measured with reference to the vacuum level. The latter parameters are usually different from the former parameters, which are obtained from solution.

As indicated above, the organic solvent-soluble compositions of this invention comprise one or more aromatic, non-polymeric amic acid salts that can be converted with thermal energy at relatively low temperatures to provide organic semiconductor compositions having one or more of the corresponding arylene diimides compounds. In many embodiments, the organic semiconductor layer consists essentially of the one or more arylene diimide compounds, meaning that no other components are present that are essential to semiconductivity, and such compounds are derived from compositions that consist essentially of the noted aromatic, non-polymeric amic acid salts. Still other embodiments have thin film semiconductor layers that consist only of the one or more arylene diimide compounds, which compounds are derived from the thermal conversion of the composition that consists of the corresponding aromatic, non-polymeric amic acid salts.

The aromatic, non-polymeric amic acid salt compositions of this invention offer several advantages. For example, since the aromatic, non-polymeric amic acid salts are soluble in a number of organic solvents, and they can be deposited on the surface of a given substrate from a suitable organic solvent solution without any additional surface preparation (for example, surface energy matching). In cases where the substrate is polymeric, the solutions can be prepared using organic solvents or mixtures of solvents that do not have unfavorable or undesirable interaction (for example, swelling) with the substrate. As noted above, the aromatic, non-polymeric amic acid salts can be quickly and easily converted to the arylene diimides at relatively low temperatures due to the presence of the catalytic cation portion of the salt.

Thus, the aromatic, non-polymeric amic acid salts have a suitable amic acid anion and one or more suitable cations. Useful cations can be organic or inorganic although the organic cations are generally best because they are more readily decomposed during the thermal conversion of the aromatic, non-polymeric amic acid salt to an arylene diimide. Useful inorganic cations include but are not limited to, alkali metal ions.

A number of organic cations can be used as counter ions to amic acid salt anions. Useful organic cations include but are not limited to, sulfonium, ammonium, phosphonium, arsenonium, morpholinium, pyridinium, quinolinium, and other organic cations that would be apparent to one skilled in the art. Quaternary ammonium ions having one to four hydrogen atoms are particularly useful and one to three valences of the cation can be filled with the same or different organic substituents such as alkyl, cycloalkyl, aryl, heteroaryl, fluoroalkyl, or heterocyclyl groups. In most embodiments, the ammonium cations have at least one hydrogen atom and up to three alkyl or cycloalkyl groups. In still other embodiments, the ammonium cations have three or four hydrogen atoms and optionally one alkyl group (such as a methyl or ethyl group) or an aryl group (such as a phenyl group).

In many embodiments of this invention, the aromatic, non-polymeric amic acid salts are represented by either the following Structure (I) or (II):

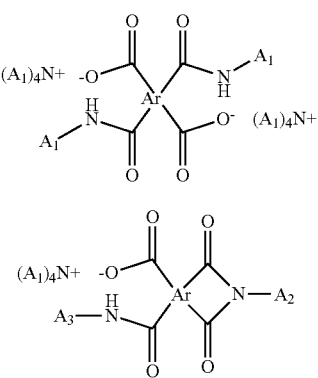

wherein: Ar is an anthracene, naphthalene, or perylene nucleus and the four carbonyl groups are attached directly to peri carbon atoms, the non-cation $A_1$, $A_2$, and $A_3$ groups are independently aryl, heteroaryl, non-aromatic alkyl, alkylaryl, fluoroalkyl, cycloalkyl, or heterocyclyl groups, and the four $A_1$ groups in the cations represent the same or different hydrogen atom or aryl, heteroaryl, non-aromatic alkyl, alkylaryl, fluoroalkyl, cycloalkyl, or heterocyclyl groups, and at least one of the $A_1$ cation groups can be a hydrogen atom.

More specifically, Ar is a substituted or unsubstituted anthracene, naphthalene, or perylene nucleus and the four carbonyl groups are attached directly to peri carbon atoms.

The non-cation $A_1$, $A_2$, and $A_3$ groups can be a substituted or unsubstituted aryl group having 6 or 14 carbon atoms in the aromatic ring (such as substituted or unsubstituted phenyl or naphthyl groups), a heteroaryl group having 5 to 10 carbon and heteroatoms (such as nitrogen, oxygen, and sulfur) in the aromatic ring (such as substituted or unsubstituted thienyl, furanyl, pyridyl, pyrrolyl, and pyrazolyl groups), a branched or linear, substituted or unsubstituted alkyl group having 1 to 18 carbon atoms and including substituted or unsubstituted fluoroalkyl groups (such as $CF_3$ or $C_3F_7$) and alkylaryl groups (such benzyl groups), a substituted or unsubstituted cycloalkyl group having at least 4 carbon atoms in the carbocyclic ring, or a substituted or unsubstituted heterocyclyl group having 5 to 10 carbon and heteroatoms (such as nitrogen, oxygen, and sulfur) in the heterocyclic ring.

The cation $A_1$ groups can be hydrogen or independently any of the groups defined above for the non-cation $A_1$, $A_2$, and $A_3$.

Various substituents on these Ar, $A_1$, $A_2$, and $A_3$ groups would be readily apparent to one skilled in the art but can include for example, alkyl groups having 1 to 6 carbon atoms (such as methyl, ethyl, pentyl, and hexyl groups), cyano, fluoro, and fluoroalkyl groups (such as $CF_3$).

In many embodiments, Ar is naphthalene or perylene, the non-cation $A_1$, $A_2$, and $A_3$ groups are independently alkyl, fluoroalkyl, alkylphenyl, phenyl, or cycloalkyl groups, which can be substituted or unsubstituted, and the four $A_1$ groups in the cations represent the same or different hydrogen or alkyl, fluoroalkyl, alkylphenyl, phenyl, or cycloalkyl groups, which can also be substituted, provided that at least three of the $A_1$ cation groups are hydrogen atoms.

For example, Ar can be a substituted or unsubstituted naphthalene or perylene, and $A_1$, $A_2$, and $A_3$ can be independently a substituted or unsubstituted alkyl, substituted or unsubstituted fluoroalkyl, substituted or unsubstituted alkylaryl, substituted or unsubstituted phenyl, or substituted or unsubstituted cycloalkyl group. More likely, Ar is perylene, and $A_1$, $A_2$, and $A_3$ are independently a substituted or unsubstituted alkyl group of 1 to 12 carbon atoms, phenyl, substituted or unsubstituted ($C_1$-$C_3$)alkylphenyl, substituted or unsubstituted cyclopentyl, or substituted or unsubstituted cyclohexyl group.

In still other embodiments, Ar is naphthalene or perylene and the four $A_1$ cation groups are hydrogen atoms.

For all of the Structures (I), (II), (Ia), (Ib), (IIa), and (IIb) described herein, some of the desired alkylaryl groups are described in U.S. Pat. No. 7,579,619 B2 (Shukla et al.) and U.S. Pat. No. 7,198,977 B2 (Shukla et al.) that are incorporated herein by reference. Some desirable fluorinated aryl groups are described in U.S. Pat. No. 7,326,956 B2 (Shukla et al.) that is also incorporated herein by reference.

Some desirable cycloalkyl groups are described in U.S. Pat. No. 7,422,777 B2 (Shukla et al.) and U.S. Pat. No. 7,649,199 B2 (Shukla et al.) that are incorporated herein by reference. Some desirable aryl groups are described in U.S. Pat. No. 7,629,605 B2 (Shukla et al.) that is incorporated herein by reference.

More specifically, some of the aromatic, non-polymeric amic acid salts of this invention are represented by the following Structure (Ia) or (IIa):

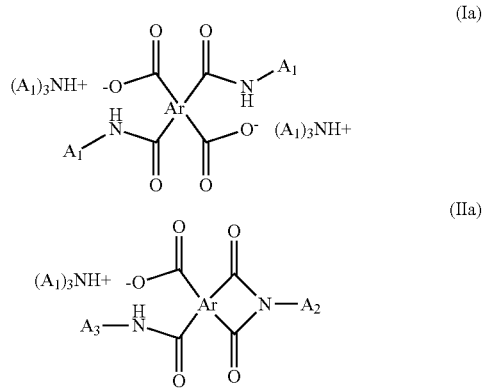

wherein: Ar and the non-cation $A_1$, $A_2$, and $A_3$ groups are as defined above, and the three $A_1$ groups in the cations represent the same or different hydrogen atom or aryl, heteroaryl, non-aromatic alkyl, alkylaryl, fluoroalkyl, cycloalkyl, or heterocyclyl groups, as defined above, provided at least one of the $A_1$ cation groups is a hydrogen atom.

Still again, the aromatic, non-polymeric amic acid salts of this invention can be represented by the following Structure (Ib) or (IIb):

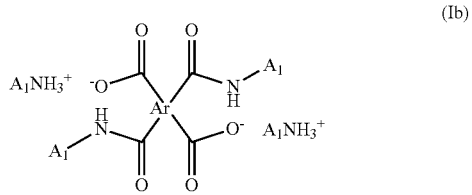

-continued (IIb)

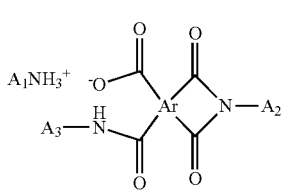

wherein: Ar and the non-cation $A_1$, $A_2$, and $A_3$ groups are as defined above, and the $A_1$ group in the cations represent a hydrogen atom or an aryl, heteroaryl, non-aromatic alkyl, alkylaryl, fluoroalkyl, cycloalkyl, or heterocyclyl groups.

In some embodiments of the Structure IIa and IIb compounds, Ar is naphthalene or perylene, the non-cation $A_1$, $A_2$, and $A_3$ groups are the same or different alkyl, fluoroalkyl, alkylphenyl, phenyl, or cycloalkyl groups, the cation $A_1$ group is a hydrogen atom or an alkyl group having 1 to 18 carbon atoms (including a methyl or ethyl group).

Examples of aromatic, non-polymeric amic acid salts of this invention are those listed below as Compounds I-1 through I-58, all of which can be thermally converted to the corresponding arylene diimides:

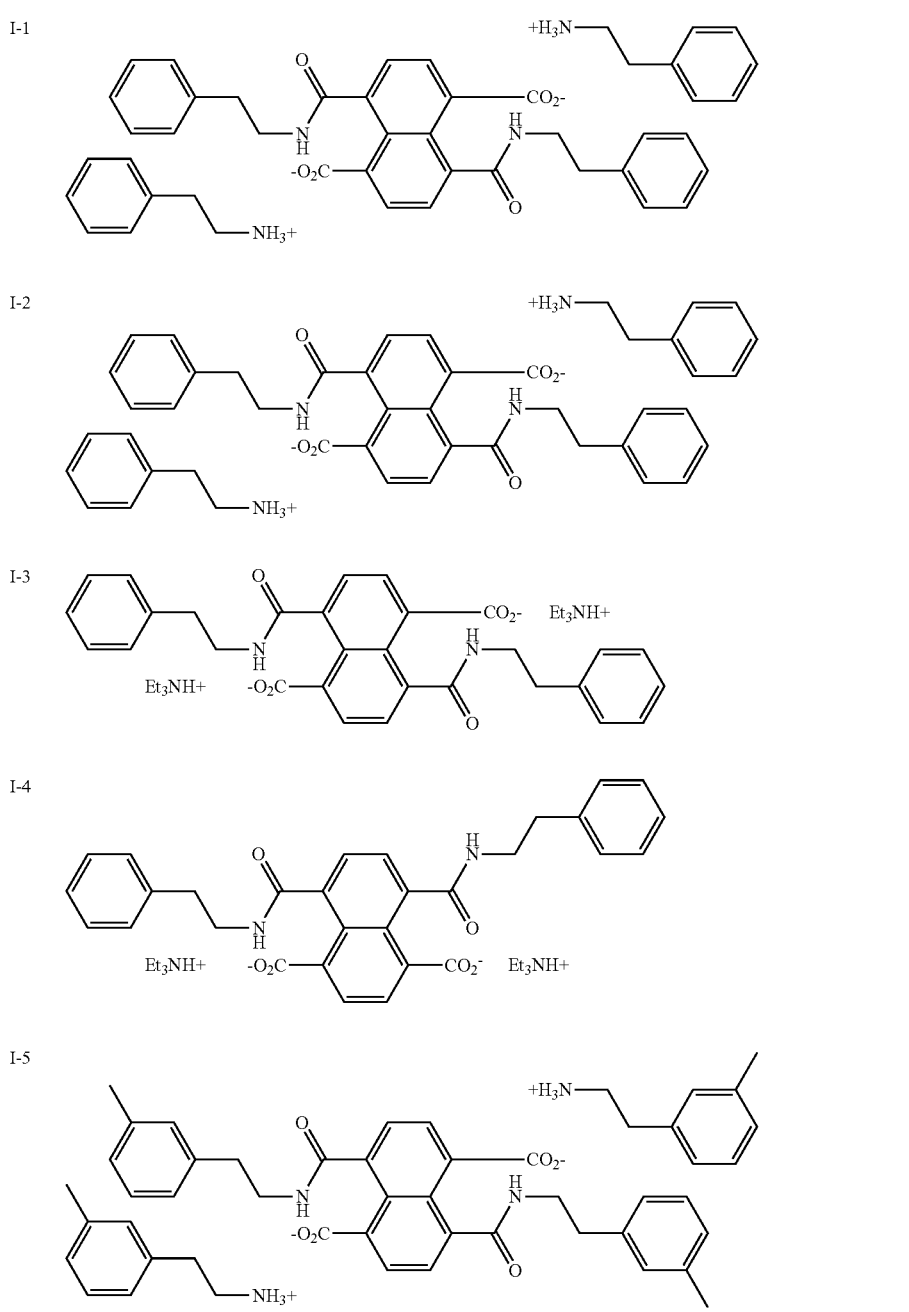

-continued
I-6
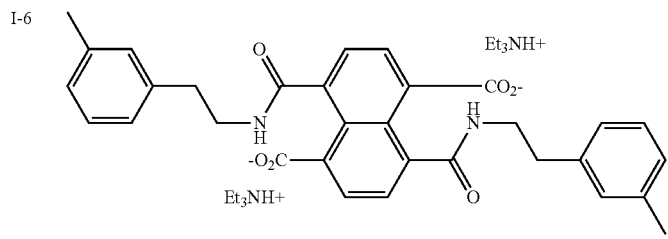
I-7
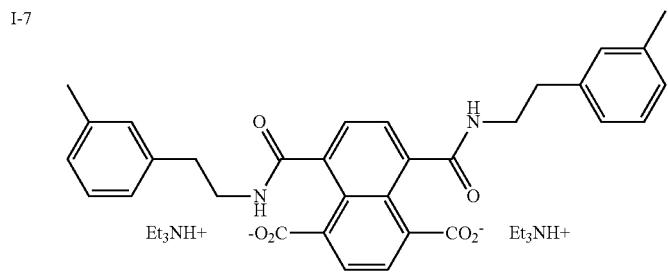
I-8
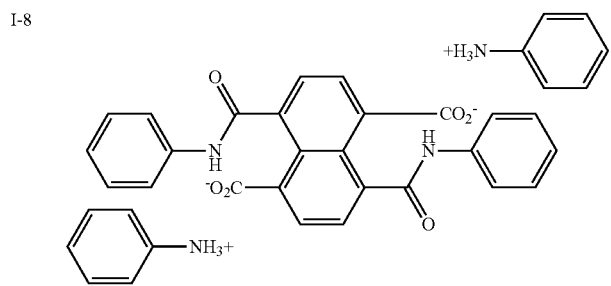
I-9
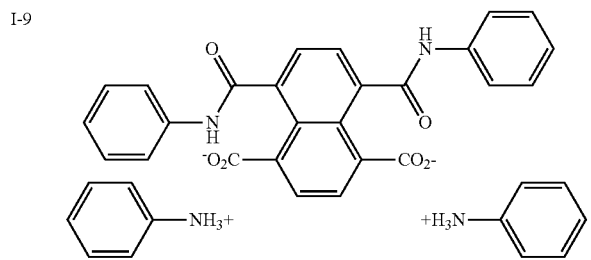
I-10
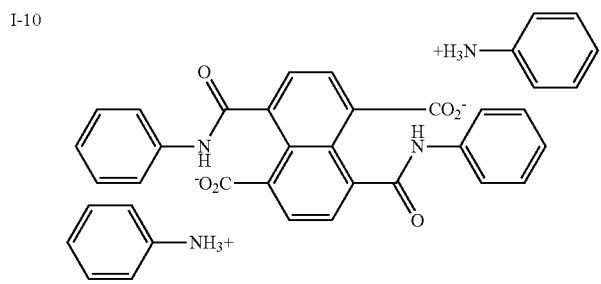
I-11
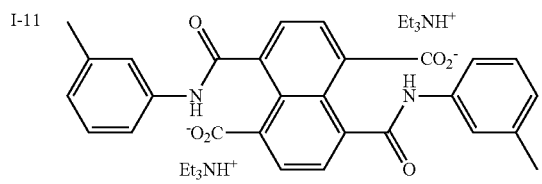

I-12 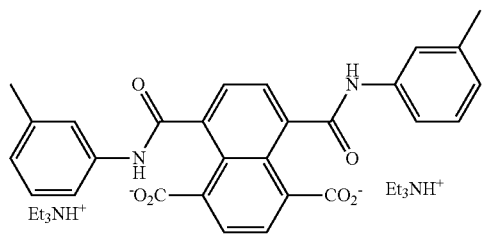
I-13 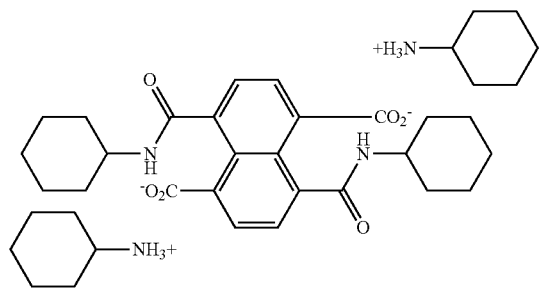
I-14 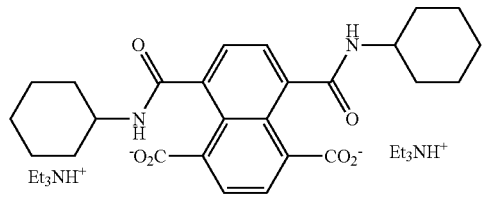
I-15 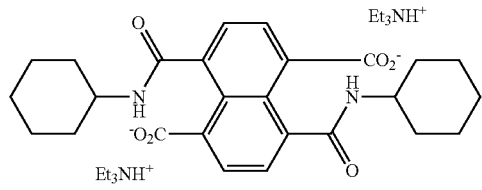
I-16 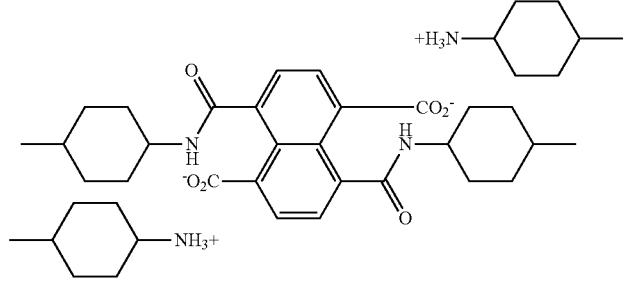
I-17 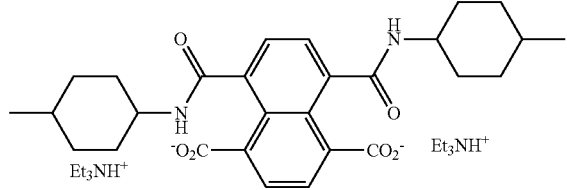
I-18 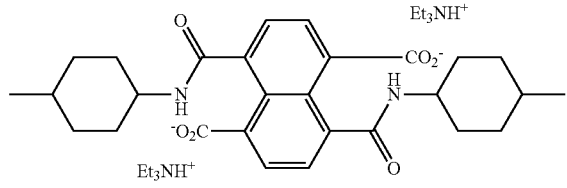

-continued
I-19
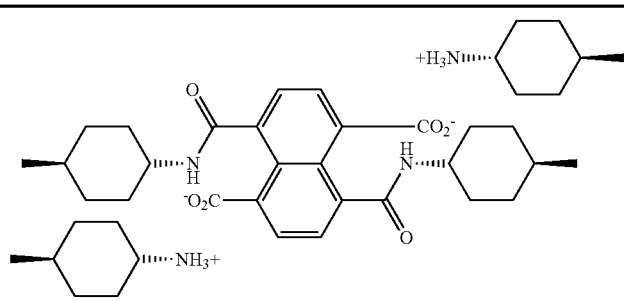
I-20
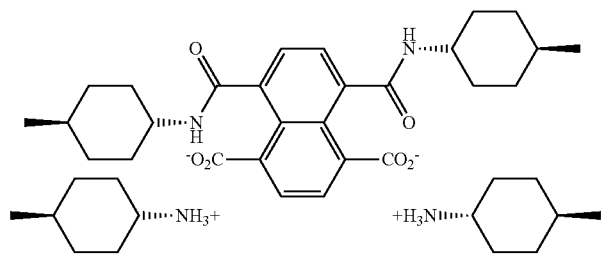
I-21
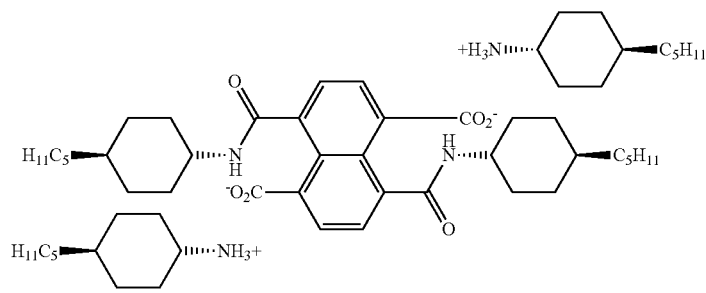
I-22
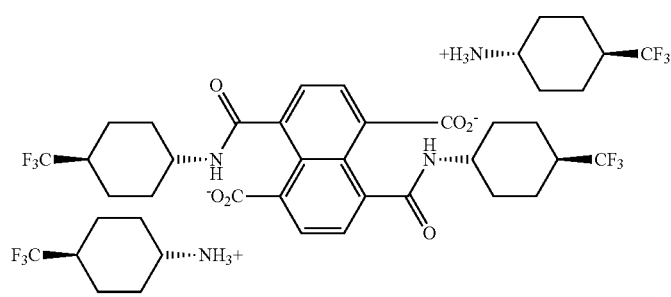
I-23
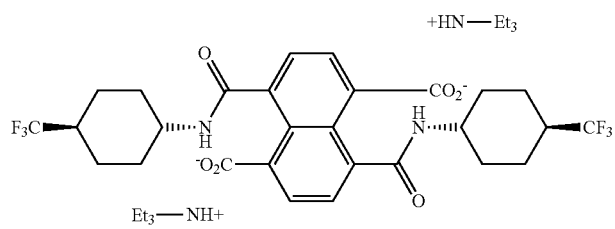
I-24
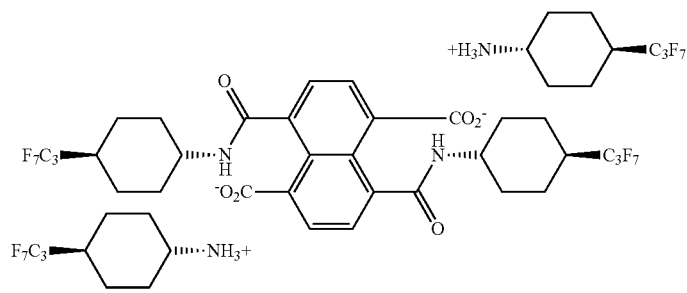

I-25
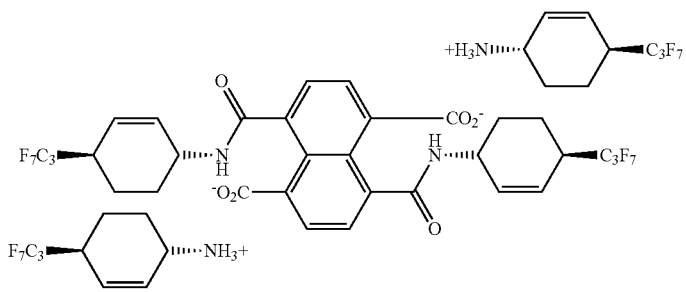
I-26
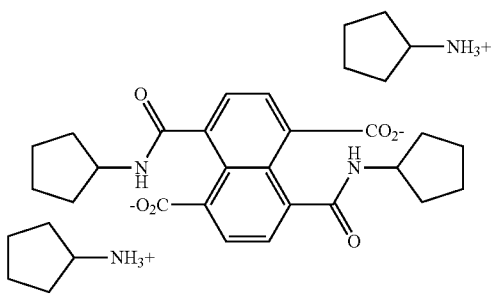
I-27
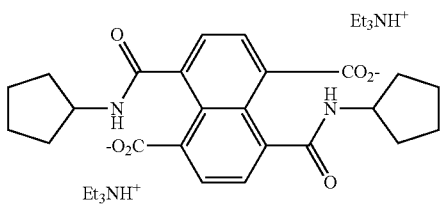
I-28
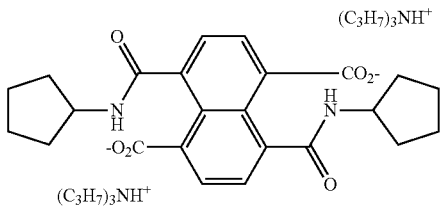
I-29
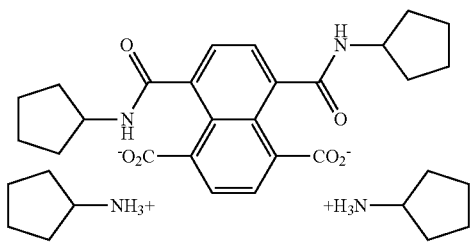
I-30
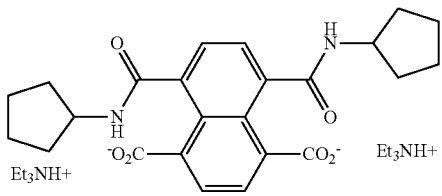

-continued
I-31 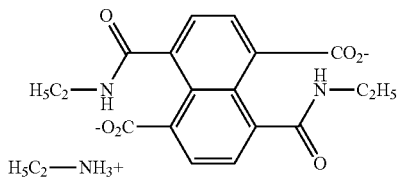
I-32 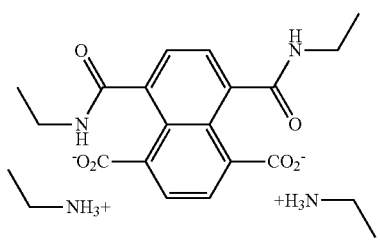
I-33 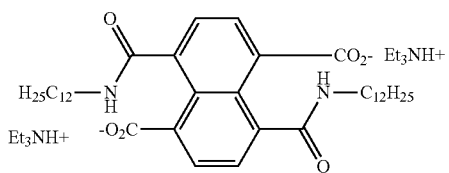
I-34 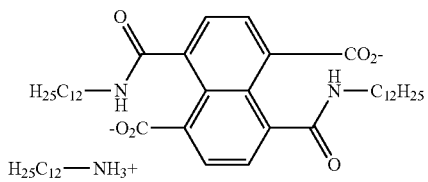
I-35 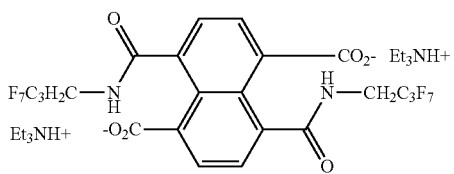
I-36 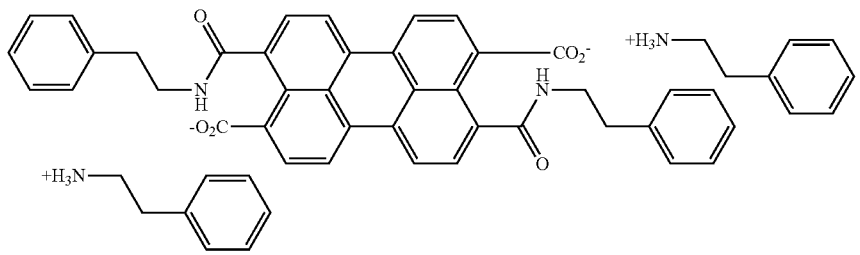
I-37 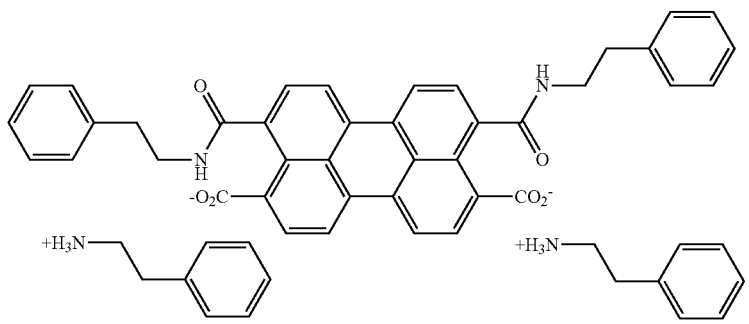

I-38
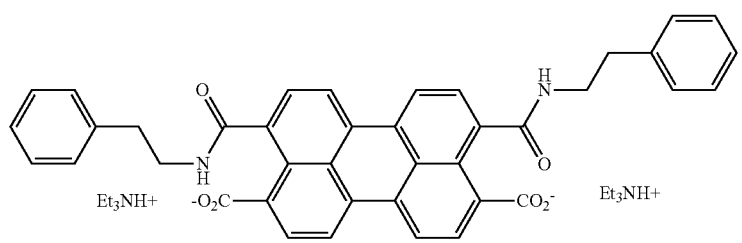
I-39
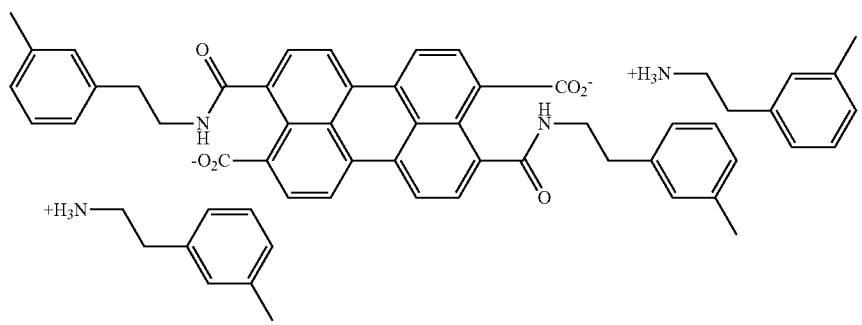
I-40
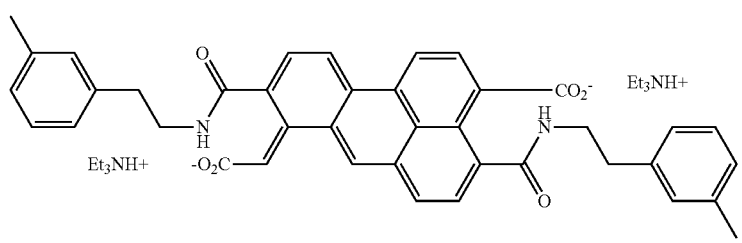
I-41
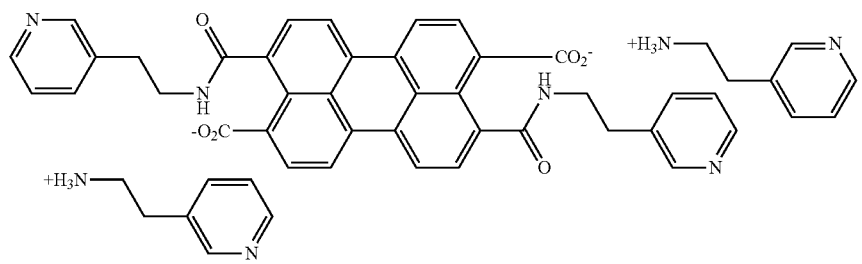
I-42
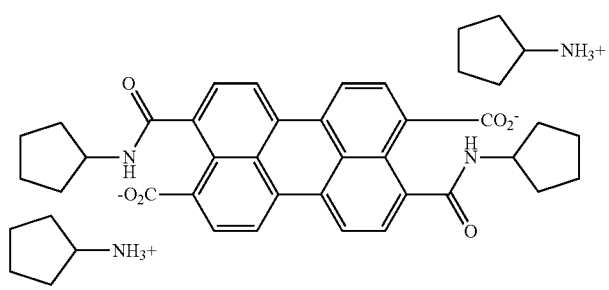
I-43
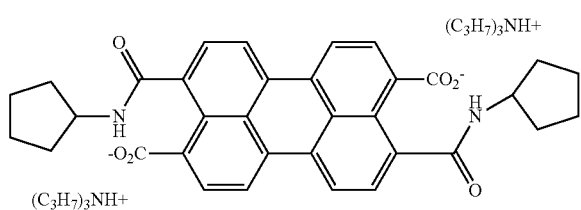

-continued
I-44
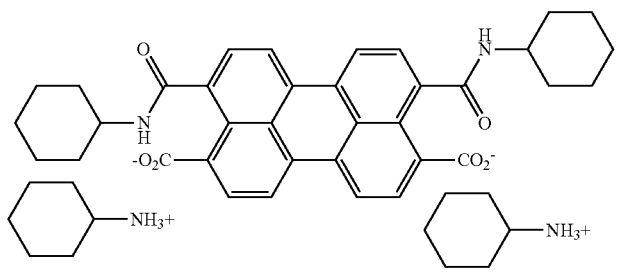
I-45
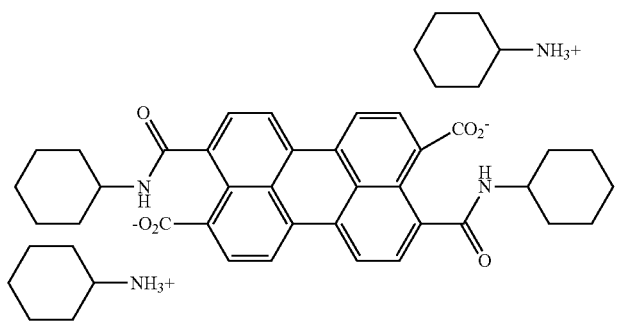
I-46
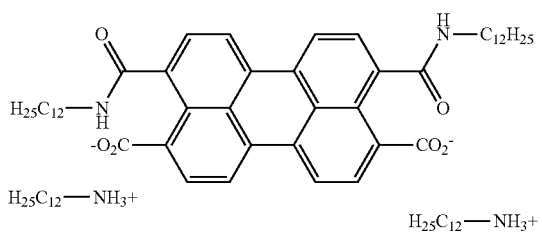
I-47
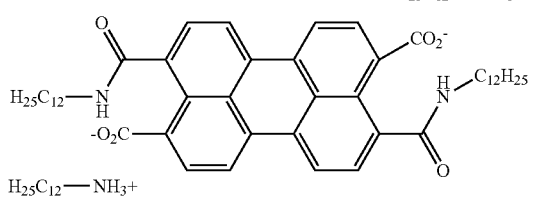
I-48
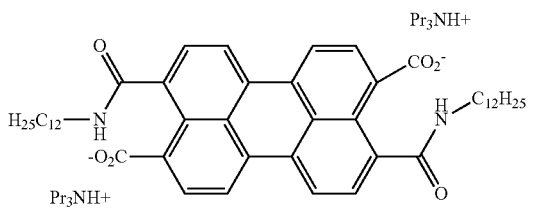
I-49
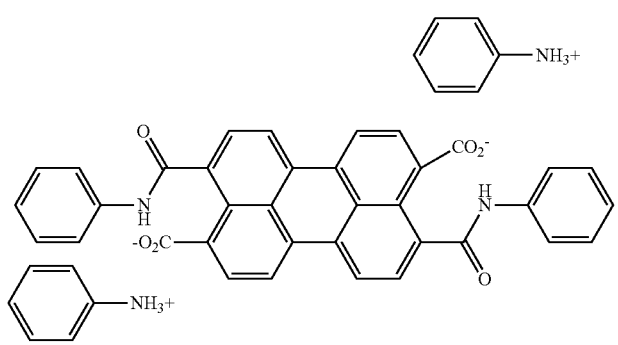

-continued
I-50
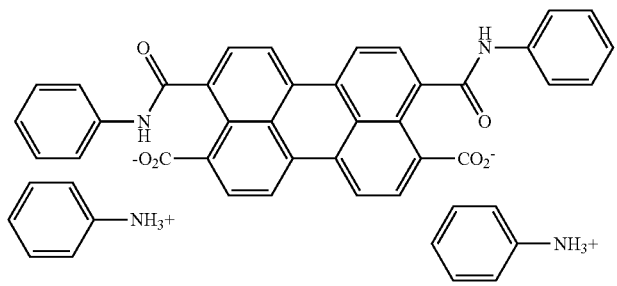
I-51
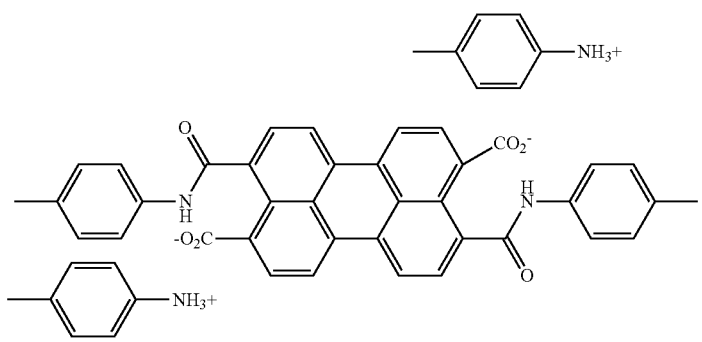
I-52
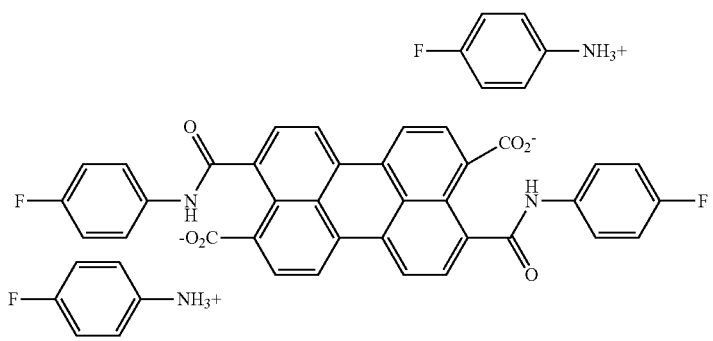
I-53
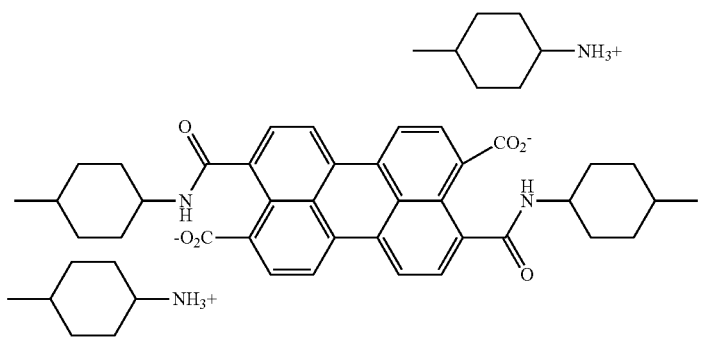
I-54
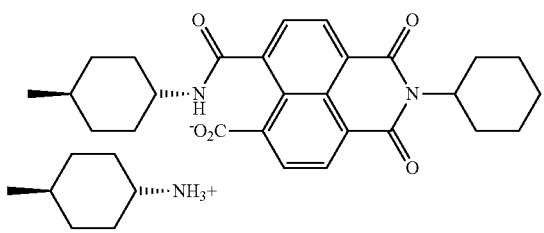

I-55
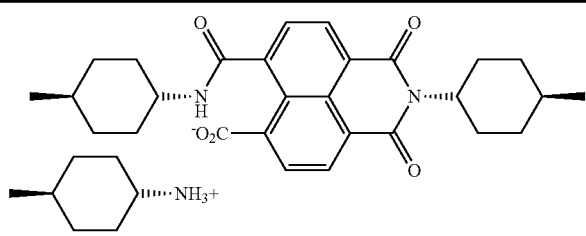

I-56
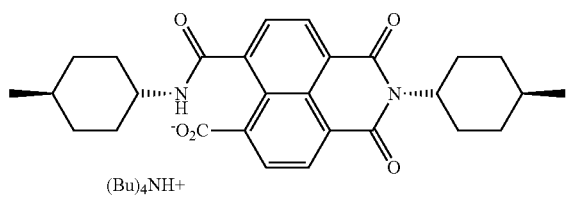

(Bu)₄NH+

I-57
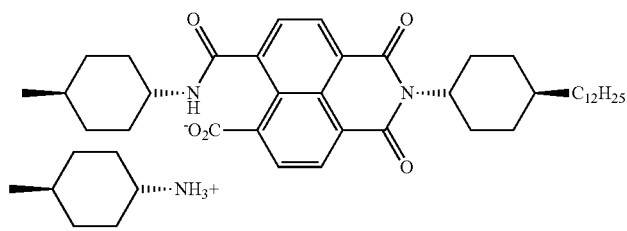

I-58
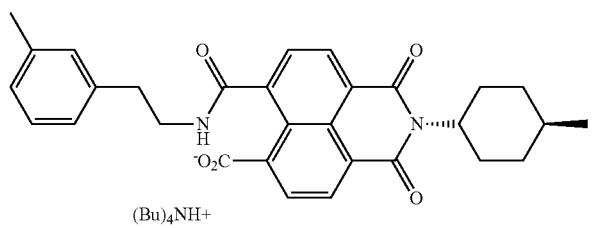

(Bu)₄NH+

The amic acid salts of this invention can be easily prepared in a simple reaction scheme, and the syntheses of several compounds are described below in the Invention Examples.

Aromatic, non-polymeric amic acid salts of general Structure Ib shown above can be prepared by a simple, one-step reaction scheme shown in the following Equation 1:

(Eq. 1)
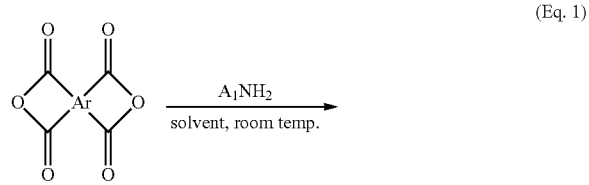

For example, bis-naphthalamic acid can be prepared by reacting an appropriate amine (such as a primary amine) with naphthalene dianhydride or the corresponding naphthalene tetracarboxylic acid with a stoichiometric excess (at least 4 equivalents) of an appropriate amine at ambient temperature in a suitable solvent or mixture of solvents. The amine is provided in a stoichiometric "excess" beyond that needed to completely use up the amine to form an amic acid salt. The excess amine in the reaction will create an aromatic, non-polymeric amic acid salt. Similar reactions can be easily carried out using other bisanhydrides and carboxylic acids.

In another method, the aromatic, non-polymeric amic acid salt of general Structure Ia shown above can be prepared by preparing the corresponding bis-amic acid followed by reaction with 2 equivalents of an appropriate amine to make the aromatic, non-polymeric amic acid salt as shown in the following Equation 2:

(Eq. 2)
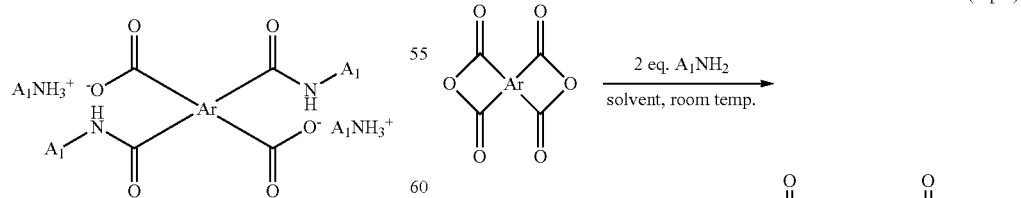

-continued

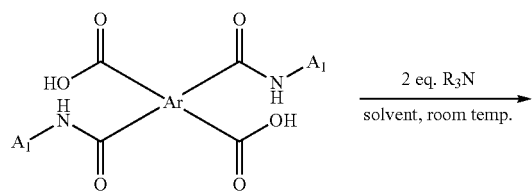

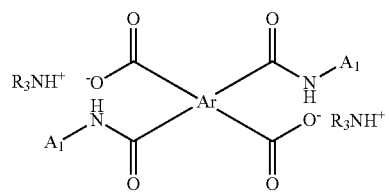

A number of organic solvents can be used for the reactions of the tetracarboxylic acid or dianhydride with the excess amine, and the choice of solvent is not particularly limited so long as it dissolves the aromatic, non-polymeric amic acid salt product. Solubility of the aromatic, non-polymeric amic acid salt depends on the nature of associated cation and can be controlled by modifying the counter cation. Specific examples of useful solvents for preparing aromatic, non-polymeric amic acid salts include, but not limited to, methanol, ethanol, n-propanol, n-butanol, N,N-dimethylformamide, N,N-dimethylacetamide, N-methyl-2-pyrrolidone, N-methylcaprolactam, dimethyl sulfoxide, tetramethylurea, pyridine, dimethyl sulfone, hexamethyl sulfoxide, γ-butyrolactone, tetrahydrofuran, chloroform, methylene chloride, dichloroethane, acetone, ethyl methyl ketone, cyclopentanone, cyclohexanone, and anisole. These solvents can be used alone or in combination. In some instances, even an organic solvent in which the aromatic, non-polymeric amic acid salt is precipitated can be used.

The aromatic, non-polymeric amic acid salt can be present in the composition of this invention in an amount of at least 0.5 weight % and up to and including 100 weight %, or from 0.5 weight % to 50 weight %. This weight % can be considered "% solids" in the compositions that are in solution form.

In the preparation of the aromatic, non-polymeric amic acid salts of this invention, both the cis and trans isomers of the aromatic, non-polymeric amic acid salts can be formed as shown in the following Equation 3:

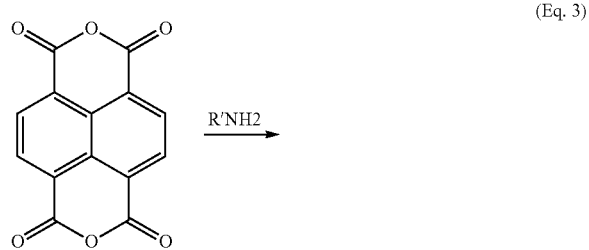
(Eq. 3)

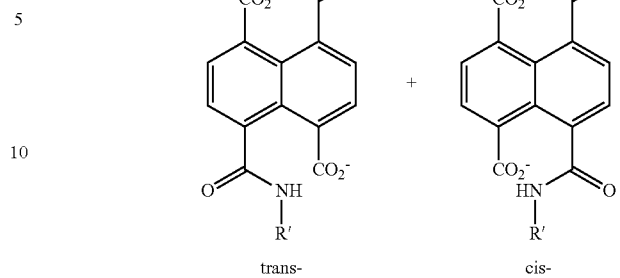

The relative amounts of cis and trans isomers depends on a number of factors such as reaction solvent, temperature, concentration of amine, and the presence or absence of additional catalyst.

To facilitate the reaction of the tetracarboxylic acid or dianhydride with an amine in the organic solvent, the amine can be dispersed or dissolved in the organic solvent, under stirring, and the tetracarboxylic acid or dianhydride is then added, as it is or after dispersing or dissolving it in the organic solvent. Alternatively, the amine can be added to a solution of the tetracarboxylic dianhydride that is dispersed or dissolved in the organic solvent. In still another method, the tetracarboxylic dianhydride and the amine can be added simultaneously to the organic solvent. In addition, the two reactants can be added alternatively to the organic solvent until all of the desired amounts are in the solution or dispersion. Stirring or other suitable agitation may be desirable to obtain a solution or dispersion of the reactants. A skilled worker would understand that still other procedures can be used to obtain the desired reaction product (aromatic, non-polymeric amic acid salt).

For the preparation of the aromatic, non-polymeric amic acid salts of Structure Ib, the molar ratio of the amine reactant (that is, the total moles of the amine to the tetracarboxylic acid or dianhydride) is generally at least 4:1, or at least 5:1, or more likely at least 6:1. For the preparation of the aromatic, non-polymeric amic acid salts of Structure IIb, the molar ratio of the amine reactant (that is, the total moles of the amine to the tetracarboxylic acid or dianhydride) is generally at least 2:1, or at least 2.2:1, or more likely at least 2.5:1.

For the preparation of the aromatic, non-polymeric amic acid salts of Structure Ia (as depicted in Equation 2), the molar ratio of the amine reactant (that is, the total moles of the amine to the tetracarboxylic acid or dianhydride) in step 1 is generally at least 2:1, or at least 2.2:1, or more likely at least 2.5:1. In step 2 for the preparation of aromatic, non-polymeric amic acid salts of Structure Ia, the molar ration of the amine reactant (that is, the total moles of the amine reactant to the aromatic, non-polymeric amic acid) is generally 2:1, or at least 3:1, or more likely at least 4:1.

Depending on the nature of the amine and dianhydride or carboxylic acid, the described synthesis of the aromatic, non-polymeric amic acid salt can be carried out at very low temperatures (from −20° C. to 0° C.), at room temperature, or at a higher temperature of from 25° C. to 100° C. The reaction of bisanhydride with the amine according to Equation 1 proceeds to give the aromatic, non-polymeric amic acid salt in high yield. For this reason, the reaction can easily be scaled up to any desired concentration. Accordingly, the concentration of the resulting product is generally from 1 to 50 weight % or from 5 to 30 weight %, or even from 1 to 10 weight % in the reaction solution or dispersion. The reaction can be carried out at a high concentration in the initial stage, and thereafter, more organic solvent, water, or both, can be added to the reaction solution or dispersion to adjust the concentration.

The aromatic, non-polymeric amic acid salt is easily converted to the corresponding arylene diimide compound by thermal dehydration imidation ring closure reaction. The temperature of the dehydration imidation ring closure is dependent on the structure of the aromatic, non-polymeric amic acid salt. However, the thermal imidation of the amic acid salt in a thin film transistor device or other article is generally carried out in the solid state at a temperature of from 100° C. and up to about 400° C., or from about 120° C. to about 250° C.

It can be advantageous to carry out the dehydration imidation ring closure reaction of aromatic, non-polymeric amic acid salt in the presence of an added catalyst in the reaction solution or dispersions. Such catalysts include be are not limited to basic catalysts such as amines such as a tertiary amine or aromatic amine. Such tertiary amines and aromatic amines include but are not limited to, pyridine, triethylamine, tributylamine, trimethylamine, tripropylamine, diazabicyclo[1.1.1]octane, diazabicycloundecane, and trioctylamine. Mixtures of these compounds can also be used. Catalytic imidation that proceeds at a relatively low temperature is particularly desirable. Such a tertiary amine or aromatic amine can be present in an amount of at least 0.5 weight % and up to and including 10 weight %, or more likely from about 0.5 to about 2 weight %, based on the amic acid salt that is to be thermally converted. Thus, the composition of this invention can consist essentially of an aromatic, non-polymeric amic acid salt and an amine such as a tertiary amine.

In some embodiments, a thin film of an arylene diimide compound can be prepared with a method comprising the steps of:

A) adding a dianhydride (as described above) to an organic solvent (described above) and stirring the resulting mixture to obtain a solution or dispersion, B) adding an amine to the dianhydride solution or dispersion to provide a molar ratio of the amine to the dianhydride of at least 4:1 and mixing the reactants to obtain an arylene diimide precursor that is an aromatic, non-polymeric amic acid salt, C) adding an amine in an amount of from 0.5 to 2 weight % to the aromatic, non-polymeric amic acid salt solution, D) applying the solution of Step C to a suitable substrate (as described below and particularly a metal, silicon, plastic film, glass sheet, or coated glass) to form a coating, E) removing the organic solvent from the coating to form a thin film of the aromatic, non-polymeric, amic acid salt, and F) thermally converting (as described above) the aromatic, non-polymeric amid acid salt precursor in the thin film to an arylene diimide compound to form an organic semiconductor layer that is generally a thin film of from about 100 to about 1000 Angstroms in dry thickness.

The solvent, or mixture of solvents, can be removed in step D using any suitable technique and equipment. Generally, the solvents are removed from the coating by a suitable evaporation technique at desired time and temperature. Higher temperatures can be used in shorted times, but it depends upon the vapor pressure of the organic solvents.

A method for preparing a thin film of an aromatic, non-polymeric amic acid salt also comprises the steps of:

A) adding a dianhydride to an organic solvent and stirring the resulting mixture to obtain a solution or dispersion, B) adding an amine to the dianhydride solution or dispersion to provide a molar ratio of the amine to the dianhydride of at least 4:1 and mixing the reactants to obtain an arylene diimide precursor that is an aromatic, non-polymeric amic acid salt, C) applying the dianhydride solution to a substrate (as described below) to form a coating (or thin film), and D) removing the organic solvent from the coating to form a layer (or thin film) of the aromatic, non-polymeric amic acid salt precursor, for example by evaporation or other technique as described above.

The resulting thin film of the aromatic, non-polymeric amic acid salt (or mixture of aromatic, non-polymeric amic acid salts) can then be further processed or used in a suitable manner before it is thermal converted to the corresponding arylene diimide compound.

More particularly, a method comprises, not necessarily in order, the following steps:

A) providing an electrically conductive substrate (as described below),

B) providing a gate electrode material over the substrate,

C) providing a gate dielectric over the gate electrode material,

D) depositing a organic solvent solution or dispersion of an aromatic, non-polymeric amic acid salt over the gate dielectric, and E) evaporating the organic solvent to produce a thin film of the aromatic, non-polymeric amic acid salt.

Thin films of the aromatic, non-polymeric amic acid salt can be cast or coated from solution in which they are prepared and they can be converted to the arylene diimide compound as a thin film by simply heating the substrate on which it is coated.

The aromatic, non-polymeric amic acid salt can be applied or deposited onto a suitable support using any suitable technique and equipment. For example, it can be applied out of the solution using solution coating techniques (such as spin or hopper coating), solution-phase deposition, ink jet techniques, lithographic or flexographic deposition in desired patterns, or spray coating.

Thermal Conversion of Precursor to Semiconductive Compound

The thermal conversion can be carried out using various procedures and apparatus to supply the desired thermal energy (or heat) to the precursor that is on a substrate. For example, the desired thermal energy can be provided by one or more lasers such as those emitting infrared radiation, microheaters, microwave heaters, and other heating devices that would be readily apparent to one skilled in the art. The thermal energy can be applied in a uniform manner over the entire applied coating of an aromatic, non-polymeric amic acid salt, or the thermal energy can be applied patternwise to convert only a pattern of the aromatic, non-polymeric amic acid salt, and the non-converted coating can then be removed in a suitable fashion (for example, by washing with a solvent in which it is soluble). As noted above, an advantage of this invention is that the aromatic, non-polymeric amic acid salts can be thermally converted at relatively lower temperatures compared to the thermal conversion temperatures of corresponding amic acids or amic esters.

Electronic Devices

The organic semiconductor composition described herein, when used in the form of an n-channel layer, can exhibit high performance under inert conditions as well as in air without the need for special chemical underlayers.

The electronic devices comprise the thin film or organic semiconductor layer as described above. The electronic devices can include, but are not limited to, an organic field effect transistor (OFET), organic light emitting diode (OLED), photodetector, sensor, logic circuit, memory element, capacitor, and photovoltaic (PV) cell. For example, the active semiconductor channel between the drain and source in an OFET can comprise the organic semiconducting layer. As another example, an electron injection or transport layer in an OLED device-can comprise the organic semiconducting layer. The amic acid salt compositions of this invention and organic semiconductor layers formed there from have particular utility in OFET's.

Thus, the compositions of this invention can be used in a process for the production of semiconductor components and electronic devices incorporating such components. In one embodiment, a substrate is provided and a layer of the aromatic, non-polymeric amic acid salt composition can be applied to the substrate and electrical contacts made with the layer. The exact process sequence is determined by the structure of the desired semiconductive article. Thus, in the production of an organic field effect transistor, for example, a gate electrode can be first deposited on a flexible substrate, for example an organic polymer film, the gate electrode can then be insulated with a dielectric and then source and drain electrodes and a layer of the aromatic, non-polymeric amic acid salt can be applied on top and then thermally converted to an n-channel semiconductor layer containing the corresponding arylene diimide compound. The structure of such a thin film transistor and hence the sequence of its production can be varied in the customary manner known to a person skilled in the art. Thus, alternatively, a gate electrode can be deposited first, followed by a gate dielectric, then the aromatic, non-polymeric amic acid salt layer can be applied, and finally the contacts for the source electrode and drain electrode deposited on the precursor layer, which is then thermally converted to an organic semiconductor layer containing the corresponding arylene diimide compound. A third structure could have the source and drain electrodes deposited first, then the aromatic, non-polymeric amic acid salt layer, with dielectric and gate electrode, is deposited on top. This layer can then be thermally converted in a suitable manner to provide the organic semiconductor arylene diimide compound.

The skilled artisan will recognize other structures can be prepared or intermediate surface modifying layers can be interposed between the above-described components of a thin film transistor device. In most embodiments, a field effect thin film transistor device comprises an insulating layer, a gate electrode, an organic semiconductor layer comprising an organic semiconducting arylene diimide compound (thermally converted from the aromatic, non-polymeric amic acid salt) as described herein, a source electrode, and a drain electrode, wherein the insulating layer, the gate electrode, the organic semiconductor layer, the source electrode, and the drain electrode are in any sequence as long as the gate electrode, and the organic semiconductor layer both contacts the insulating layer, and the source electrode and the drain electrode both contact the organic semiconductor layer.

Substrate

A substrate (also known herein as a support) can be used for supporting the organic semiconductor thin film during manufacturing, testing, or use. The skilled artisan will appreciate that a substrate selected for commercial embodiments can be different from one selected for testing or screening various embodiments. In other embodiments, a substrate can be detachably adhered or mechanically affixed to a substrate, such as when the substrate is desired for a temporary purpose. For example, a flexible polymeric substrate can be adhered to a rigid glass support, which support could be removed. In some embodiments, the substrate does not provide any necessary electrical function for the FET. This type of substrate is considered a "non-participating substrate".

Useful substrate materials can include organic or inorganic materials. For example, the substrate can comprise inorganic glasses, ceramic foils, polymeric materials, filled polymeric materials, coated metallic foils, acrylics, epoxies, polyamides, polycarbonates, polyimides, polyketones, poly(oxy-1,4-phenyleneoxy-1,4-phenylenecarbonyl-1,4-phenylene) [sometimes referred to as poly(ether ether ketone) or PEEK], polynorbornenes, polyphenyleneoxides, poly(ethylene naphthalenedicarboxylate) (PEN), poly(ethylene terephthalate) (PET), poly(phenylene sulfide) (PPS), and fiber-reinforced plastics (FRP).

A flexible substrate is used in some embodiments to allow for roll processing, which can be continuous, providing economy of scale and economy of manufacturing over flat or rigid substrates. The flexible substrate chosen is capable of be wrapped around the circumference of a cylinder of less than about 50 cm diameter, typically less than 25 cm diameter, or even less than 10 cm diameter, without distorting or breaking, using low force such as by unaided hands. The flexible substrate can be rolled upon itself.

In some embodiments of the articles, the substrate is optional. For example, in a top construction as in FIG. 1b, when the gate electrode or gate dielectric provides sufficient substrate for the intended use of the resultant TFT, the substrate is not required. In addition, the substrate can be combined with a temporary support. In such an embodiment, a substrate can be detachably adhered or mechanically affixed to the substrate, such as when the substrate is desired for a temporary purpose, for example, manufacturing, transport, testing, or storage. For example, a flexible polymeric substrate can be adhered to a rigid glass support, which flexible substrate can be removed.

Gate Electrode

The gate electrode can be any useful conductive material. A variety of gate materials known in the art, are also suitable including metals, degenerately doped semiconductors, conducting polymers, and printable materials such as carbon ink or silver-epoxy. For example, the gate electrode can comprise doped silicon, or a metal, such as aluminum, chromium, gold, silver, nickel, palladium, platinum, tantalum, and titanium. Conductive polymers also can be used, for example polyaniline, poly(3,4-ethylenedioxythiophene)/poly(styrene sulfonate) (PEDOT:PSS). In addition, alloys, combinations, and multilayers of these materials can be useful.

In some embodiments, the same material can provide the gate electrode function and also provide a support function. For example, doped silicon can function as the gate electrode and support the OFET.

Gate Dielectric

The gate dielectric is provided on the gate electrode to electrically insulate the gate electrode from the balance of the OFET device. The gate dielectric can be provided in the OFET as a separate layer, or formed on the gate such as by oxidizing the gate material to form the gate dielectric. The dielectric layer can comprise two or more layers having different dielectric constants.

The gate dielectric should have a suitable dielectric constant that can vary widely depending on the particular device and circumstance of use. For example, a dielectric constant from about 2 to about 100 or even higher is known for a gate dielectric. The gate dielectric layer should have a resistivity of $10^{14}$ ohm-cm or greater in OFET applications. The gate dielectric can comprise organic polymeric materials, inorganic materials, and organic-inorganic composite materials. Useful polymer materials for the gate dielectric can comprise one or more dielectric polymers such as acrylic and styrenic polymers selected from the group consisting of: acrylic, styrenic and styrenic-acrylic latexes, solution-based acrylic, styrenic and styrenic-acrylic polymers, and combinations thereof heteroatom-substituted styrenic polymers selected from the group consisting of: partially hydrogenated poly(4-hydroxy)styrene, poly(4-hydroxy)styrene, and copolymers of poly(4-hydroxy)styrene with hydroxyethyl(meth)acrylate, alkyl(meth)acrylate, styrene, and alkyl-substituted styrene wherein the alkyl group is a $C_1$ to $C_{18}$ straight or branched chain alkyl group, phenol-aldehyde (co)polymers and (co) oligomers and combinations thereof. The gate dielectric can comprise a polymeric material, such as poly(vinylidene difluoride) (PVDF), cyanocelluloses, polyimides, and others known in the art. The gate electric can comprise a plurality of layers of different materials having different dielectric constants.

In certain embodiments, polymer gate dielectric can possess one or more of the following characteristics: coatable out of solution, crosslinkable, photo-patternable, high thermal stability (for example, stable up to a temperature of about 250° C.), low processing temperatures (for example, less than about 150° C. or less than 100° C.), and are compatible with flexible substrates. Crosslinkable or photo-patternable polymers are particularly desirable. This is because they provide flexibility in manufacturing methods, would easily integrate with solution processed device layers, and could allow for high-speed roll-to-roll processing. Polymers are photo-patternable if they include one or more crosslinking (that is, crosslinkable) groups that can be induced to form a crosslinked network upon exposure to radiation (most commonly, UV radiation). The exposed (crosslinked portion of the polymer) becomes insoluble in certain solvents and the unexposed portion of the polymer can be washed away using a developing solvent. This is an example of a negative-acting photo-patternable polymer. It is also possible to photo-pattern a polymer that is initially insoluble in certain solvents and that becomes soluble in UV-exposed areas upon exposure. This is an example of a positive-acting photo-patternable polymer.

For OFET's, the polymeric dielectric layer generally has a thickness of less than about 5000 Angstroms (Å), typically less than about 3000 Å, or less than about 2000 Å. The polymeric dielectric layer generally has a thickness of at least about 500 Å or typically at least about 1000 Å. The thickness can be determined through known methods such as ellipsometry and profilometry. For embedded capacitors and printed circuit board applications, the thickness can include those described above for OFET's, but can also be at least 10 µm or at least 20 µm.

The term dielectric polymers herein encompasses homopolymers, copolymers derived from polymerization of two or more monomers, post-derivatized (co)polymers including graft (co)polymers, and low molecular weight homopolymers or copolymers. The polymers can be linear, branched, hyperbranched, or dendritic.

Useful materials for the gate dielectric can comprise, for example, an inorganic electrically insulating material. Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these materials can be used for the gate dielectric. In addition, polymeric materials such as polyimides and insulators that exhibit a high dielectric constant are also suitable dielectric materials as described in U.S. Pat. No. 5,981,970 (Dimitrakopoulous et al.).

Useful dielectric polymers include acrylic, styrenic, and styrenic-acrylic latexes comprising alkyl(meth)acrylate, styrene, and alkyl-substituted styrene wherein the alkyl group is a $C_1$ to $C_{18}$ straight or branched chain alkyl group. Useful optional monomers used to derive these latex-based polymers include (meth)acrylic acid, hydroxyethyl(meth)acrylate, and glycidyl(meth)acrylate. Such latexes are selected from the group: Latexes A, defined herein as one or more latex resins comprising at least 85 weight % or at least 90 weight % of alkyl(meth)acrylate, styrene, and alkyl-substituted styrene. Useful additional monomers used to derive these latex resins include (meth)acrylic acid (up to 5 weight %), hydroxyethyl (meth)acrylate (up to 10 weight %), and glycidyl(meth)acrylate (up to 5 weight %). Such latexes generally have an average particle size of less than about 150 nm or less than about 100 nm.

Particularly useful dielectric polymers with high resistivity (above $10^{14}$ ohm-cm) are Acrylic Latexes B and Styrene-Acrylic Latexes C and combinations thereof. Acrylic Latexes B are defined herein as one or more acrylic latexes comprising at least 85 weight % or at least 90 weight % of methyl methacrylate or butyl acrylate or both. Styrene-Acrylic Latexes C are defined herein as one or more styrene-acrylic latexes comprising at least 85 weight % or at least 90 weight % of methyl methacrylate, butyl acrylate, or styrene, or mixtures thereof. Useful additional monomers used to derive Acrylic Latexes B and Styrene-Acrylic Latexes C include (meth)acrylic acid (up to 5 weight %), hydroxyethyl methacrylate (up to 10 weight %), and glycidyl methacrylate (up to 5 weight %). Commercial examples of acrylic and styrenic acrylic latexes useful as dielectric polymers include Joncryl® 95 and 1915 (co)polymers (Johnson Polymer). Methods for synthesizing suitable latex polymers have been reported in WO 03/099574 (Caspar et al.).

Further useful dielectric polymers include solution-based acrylic, styrenic and styrenic-acrylic polymers. Herein the term "solution-based" refers to materials that are soluble in solvents such as water or one or more common organic solvents including alcohols, ethers, esters, ketones, and aromatic hydrocarbons. Such solution-based acrylic, styrenic and styrenic-acrylic polymers have a Mw of less than 100,000 and an acid number less than about 250.

Useful dielectric polymers also include heteroatom-substituted styrenic polymers selected from the group consisting of: partially hydrogenated poly(4-hydroxy)styrene, poly(4-hydroxy)styrene (PHS), and copolymers of PHS with hydroxyethyl(meth)acrylate, alkyl(meth)acrylate, styrene, and alkyl-substituted styrene wherein the alkyl group is a $C_1$ to $C_{18}$ straight or branched chain alkyl group. When a PHS homopolymer is used, the branched structure is desired and the (co)polymers have an Mw of less than about 30,000. Partially hydrogenated PHS refers to PHS polymers that have been hydrogenated up to about 50 equivalent % of the unsaturation within the polymer. Commercial examples include PHS-B (branched PHS homopolymer; DuPont Electronic Technologies, Dallas, Tex.), Maruka Lyncur CMM (PHS copolymer with methyl methacrylate; Maruzen Petrochemical Co., LTD. Tokyo, Japan), Maruka Lyncur CHM (PHS copolymer with hydroxyethyl methacrylate; Maruzen), Maruka Lyncur CBA (PHS copolymer with butyl acrylate, Maruzen), Maruka Lyncur CST 15, 50, and 70 (PHS copolymers with styrene, Maruzen), and Maruka Lyncur PHM-C (partially hydrogenated PHS, Maruzen).

Other useful dielectric polymers include phenol-aldehyde (co)polymers/(co)oligomers and combinations thereof that are derived from mono- and bis-phenols and mono- and bis-aldehydes selected from the group consisting of: phenol, alkyl- and aryl-substituted phenols; formaldehyde, and alkyl-, aryl- and heteroatom-substituted aldehydes. The phenol-aldehyde resins can be further derivatized, for example, the hydroxy group converted to an ether group. Such (co)polymers/(co)oligomers have an Mw of 20,000 or less or 10,000 or less. Other useful dielectric polymers include poly(vinyl acetate) homopolymers having an Mw of 100,000 or less.

The above polymers can be plasticized for improved flexibility, adhesion, compatibilization with an IR dye, among other characteristics. In certain instances, the plasticizer can be selected from the above classes of polymers. For example, a higher Tg or higher molecular weight (Mw) phenol-aldehyde polymer can be blended with a lower Tg or lower Mw phenol-aldehyde polymer. Another example is PHS blended with a phenol-aldehyde polymer. Examples of suitable plasticizers for some of the above classes of polymers comprise poly(ethylene)glycol, glycerol ethoxylate, di(ethylene glycol)dibenzoate, and phthalate-based plasticizers such as dibutyl phthalate. A number of potentially suitable plasticizers for various polymers and details regarding their use can be found in the following reference: "Handbook of Plasticizers," Ed. G. Wypych, ChemTec Publishing, Toronto, Ontario, 2004.

Source and Drain Electrodes

The source electrode and drain electrode are separated from the gate electrode by the gate dielectric while the organic semiconductor layer can be over or under the source electrode and drain electrode. The source and drain electrodes can be any useful electrically conductive material including but not limited to, those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof.

The thin film electrodes (for example, gate electrode, source electrode, and drain electrode) can be provided by any useful means such as physical vapor deposition (for example, thermal evaporation, sputtering) or ink jet printing. The patterning of these electrodes can be accomplished by known methods such as shadow masking, additive photolithography, subtractive photolithography, printing, microcontact printing, and pattern coating.

The organic semiconducting layer can be located over or under the source and drain electrodes, as described above in reference to the thin film transistor articles. Useful articles can also include an integrated circuit comprising a plurality of OFET's made by the process described herein. The n-channel organic semiconductor layer containing the above-described aromatic, non-polymeric amic acid salt of this invention is capable of being formed on any suitable substrate that can comprise the support and any intermediate layers such as a dielectric or insulator material, including those known in the art.

Processing

Organic semiconductor layers can be readily prepared by solution coating of an aromatic, non-polymeric amic acid salt of this invention and after the coating solvent is removed, thermal dehydration imidization conversion of this compound in the coating to the corresponding arylene diimide compound in solid thin film form. The resulting organic semiconductor layer or the layer(s) of the gate dielectric can be deposited by spin coating. The entire process of making the thin film transistor devices or integrated circuits can be carried out below a maximum support temperature generally at or below 450° C. or typically at or below 250° C., or even at or below 200° C. The temperature selection generally depends on the nature of the aromatic, non-polymeric amic acid salt, support, and processing parameters known in the art, once a skilled artisan has the knowledge of the present invention contained herein. These temperatures are well below traditional integrated circuit and semiconductor processing temperatures that enable the use of any of a variety of relatively inexpensive supports, such as flexible polymeric supports. Furthermore, since the aromatic, non-polymeric amic acid salts are soluble in a number of solvents it affords flexibility in coating formulations and conditions. This enables production of relatively inexpensive integrated circuits containing organic thin film transistors using a significantly simplified process.

In cases where the gate dielectric is a polymer, both the organic semiconductor layer and the gate dielectric layer can be deposited from solution, making the coating of large areas less difficult. Furthermore, the aromatic, non-polymeric amic acid salts of this invention are soluble in a number of solvents, providing coating and manufacturing flexibility.

In one embodiment, an FET structure of FIG. 1a is prepared by spin coating the aromatic, non-polymeric amic acid salt layer onto the dielectric layer with pre-patterned source and drain electrodes. In another embodiment, an FET structure of FIG. 1c is prepared by spin coating the aromatic, non-polymeric amic acid salt onto the substrate with pre-patterned source and drain electrodes. Heating the layer at appropriate temperature and time converts the aromatic, non-polymeric amic acid salt to obtain the corresponding semiconductive arylene diimide compound. Next, a dielectric layer in the form of a polymer is spin coated onto the organic semiconductor layer followed by the deposition of the gate electrode by vacuum deposition or liquid deposition of a conductive metal or metal dispersion, respectively. Thermal conversion of the aromatic, non-polymeric amic acid salt to the arylene diimide compound can be accomplished as described above.

Devices in which the n-channel organic semiconductor layers described herein are useful include thin film transistors (TFT's), especially OFET's. Such layers can be used also in various types of devices having organic p-n junctions, such as the devices described on pages 13-15 of U.S. Patent Application Publication 2004/0021204 (Liu).

Electronic devices in which FET's and other devices are useful include, for example, more complex circuits such as shift registers, integrated circuits, logic circuits, smart cards, memory devices, radio-frequency identification tags, backplanes for active matrix displays, active-matrix displays (for example liquid crystal or OLED), solar cells comprising a multiplicity of thin-film transistors, ring oscillators, and complementary circuits, such as inverter circuits, for example, in combination with other transistors made using available p-type organic semiconductor materials such as pentacene. In an active matrix display, a thin film transistor device can be used as part of voltage hold circuitry of a pixel of the display. In devices containing FET's, the FET's are operatively connected in ways that are known in the art. In some embodiments, a multiplicity of thin-film transistors are deposed on a non-participating support that is optionally flexible.

The present invention provides at least the following embodiments and combinations thereof, but other combinations of features are considered to be within the present invention as a skilled artisan would appreciate from the teaching of this disclosure:

1. An organic composition that comprises an aromatic, non-polymeric amic acid salt.

2. The composition of embodiment 1 wherein the aromatic, non-polymeric amic acid salt is represented by the following Structure (I) or (II):

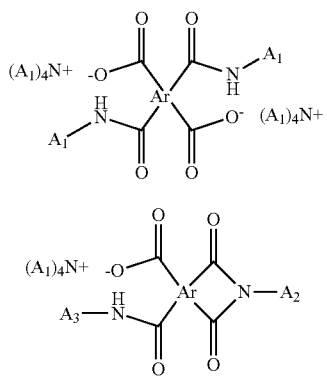

wherein: Ar is an anthracene, naphthalene, or perylene nucleus and the four carbonyl groups are attached directly to peri carbon atoms, the non-cation $A_1$, $A_2$, and $A_3$ groups are independently aryl, heteroaryl, non-aromatic alkyl, alkylaryl, fluoroalkyl, cycloalkyl, or heterocyclyl groups, and the four $A_1$ groups in the cations represent the same or different hydrogen atom or aryl, heteroaryl, non-aromatic alkyl, alkylaryl, fluoroalkyl, cycloalkyl, or heterocyclyl groups, provided at least one of the $A_1$ cation groups is a hydrogen atom.

3. The composition of embodiment 2 wherein Ar is naphthalene or perylene, the non-cation $A_1$, $A_2$, and $A_3$ groups are independently alkyl, fluoroalkyl, alkylphenyl, phenyl, or cycloalkyl groups, and the four $A_1$ groups in the cations represent the same or different hydrogen or alkyl, fluoroalkyl, alkylphenyl, phenyl, or cycloalkyl groups, provided that at least three of the $A_1$ cation groups are hydrogen atoms.

4. The composition of embodiment 2 or 3 wherein Ar is naphthalene or perylene and the four $A_1$ cation groups are hydrogen atoms.

5. The composition of embodiment 1 wherein the aromatic, non-polymeric amic acid salt is represented by the following Structure (Ia) or (IIa):

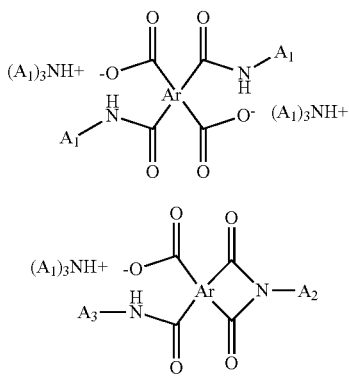

wherein: Ar is an anthracene, naphthalene, or perylene nucleus and the four carbonyl groups are attached directly to peri carbon atoms, the non-cation $A_1$, $A_2$, and $A_3$ groups are independently aryl, heteroaryl, non-aromatic alkyl, alkylaryl, fluoroalkyl, cycloalkyl, or heterocyclyl groups, and the three $A_1$ groups in the cations represent the same or different hydrogen atom or aryl, heteroaryl, non-aromatic alkyl, alkylaryl, fluoroalkyl, cycloalkyl, or heterocyclyl groups, provided at least one of the $A_1$ cation groups is a hydrogen atom.

6. The composition of embodiment 1 wherein the aromatic, non-polymeric amic acid salt is represented by the following Structure (Ib) or (IIb):

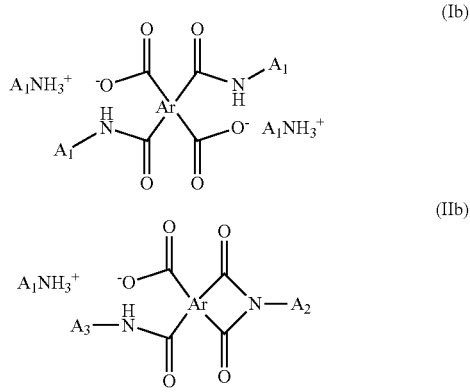

wherein: Ar is an anthracene, naphthalene, or perylene nucleus and the four carbonyl groups are attached directly to peri carbon atoms, the non-cation $A_1$, $A_2$, and $A_3$ groups are independently aryl, heteroaryl, non-aromatic alkyl, alkylaryl, fluoroalkyl, cycloalkyl, or heterocyclyl groups, and the $A_1$ group in the cations represent a hydrogen atom or an aryl, heteroaryl, non-aromatic alkyl, alkylaryl, fluoroalkyl, cycloalkyl, or heterocyclyl groups.

7. The composition of embodiment 6 wherein Ar is naphthalene or perylene, the non-cation $A_1$, $A_2$, and $A_3$ groups are the same or different alkyl, fluoroalkyl, alkylphenyl, phenyl, or cycloalkyl groups, the cation $A_1$ group is a hydrogen atom or an alkyl group.

8. The composition of embodiment 6 or 7 wherein the cation $A_1$ group is a hydrogen atom.

9. The composition of any of embodiments 1 to 8 including one or more organic solvents in which the aromatic, non-polymeric amic acid salt is soluble or dispersible.

10. The composition of embodiment 9 wherein the aromatic, non-polymeric amic acid salt is present in an amount of at least 0.5 and up to and including 50 weight % based on total composition weight.

11. The composition of any of embodiments 1 to 10 that consists essentially of the aromatic, non-polymeric amic acid salt and an amine catalyst.

12. The composition of any of embodiments 1 to 10 that consists only of the aromatic, non-polymeric amic acid salt.

13. The composition of any of embodiments 1 to 12 wherein the aromatic, non-polymeric amic acid salt is one or more of Compounds I-1 through I-58 that are described above.

The present invention is demonstrated by the following examples that are intended to be exemplary and not limiting in any manner.

Invention Example 1

Preparation of di-(cyclopentylammonium)-4,8-bis(cyclopentylcarbamoyl)-naphthalene-1,5-dicarboxylate as a Mixture of trans-and cis-isomers (Compounds I-26 and I-29)

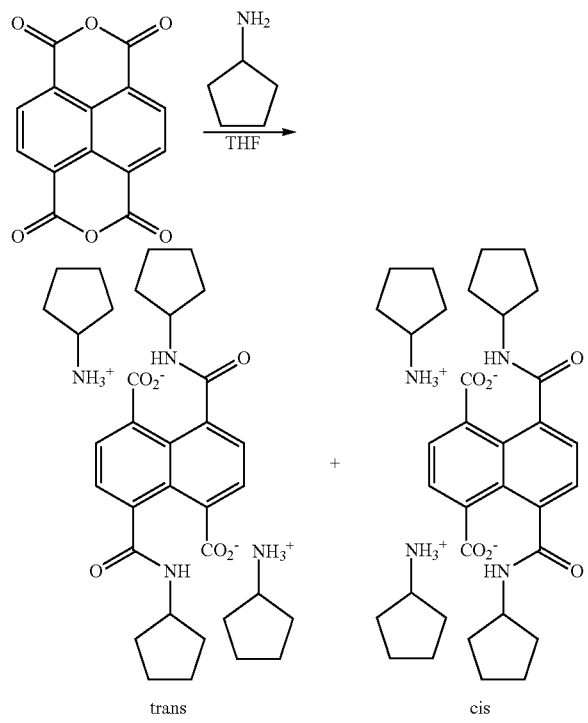

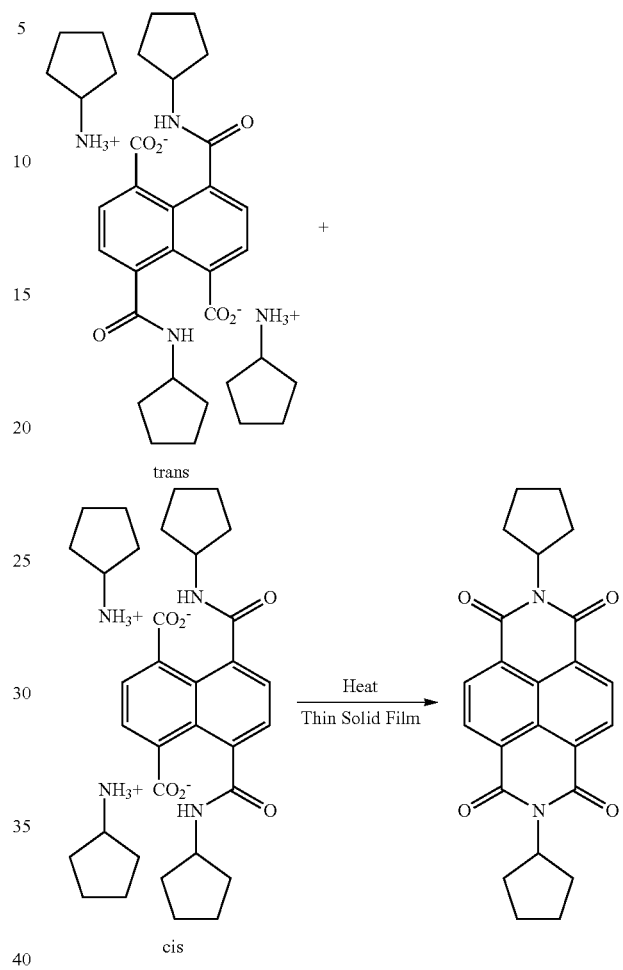

To a stirred dispersion of 1,4,5,8-naphthalene tetracarboxylic acid dianhydride (46 mg) in tetrahydrofuran (4 ml), a solution of cyclopentylamine (mg) in tetrahydrofuran (1 ml) was added dropwise to obtain first a clear pale yellow solution that quickly turned cloudy. Stirring was continued for an additional 5 minutes then excess diethyl ether was added to obtain a precipitate that was filtered, washed with diethyl ether, and dried in air.

$^1$H and $^{13}$C NMR spectra of the product were consistent with the salt being a mixture of cis and trans isomers. The aromatic protons of the trans-isomer appeared as a two doublets at 7.79 ppm (J=7.60 Hz) and 7.63 ppm (J~7 Hz); aromatic protons of the cis isomer appeared as singlets at 7.81 ppm and 7.62 ppm. From the integrated areas of the aromatic protons, it was determined that the product was a 1:1 mixture of cis and trans amic acid salt. $^1$H NMR (CD$_3$OD, 300 MHz) δ(ppm)=7.81 ppm (s, 2H, cis isomer), 7.79 (2H, J=7.60 Hz, trans isomer), 7.63 (s, 2H, J=7 Hz, trans isomer), 7.62 (s, 2H, cis isomer), 4.28 (m, 2H), 3.48 (m, 2H), 2 (m, 8H), 1.63 (m, 26H). $^{13}$C NMR (CD$_3$OD) δ(ppm)=174.99, 170.98, 139.81, 137.82, 136.54, 128.48, 127.11, 126.82, 126.26, 126.06, 51.97, 32.30, 30.88, 23.74, 23.69.

Invention Example 2

Figure 2B:
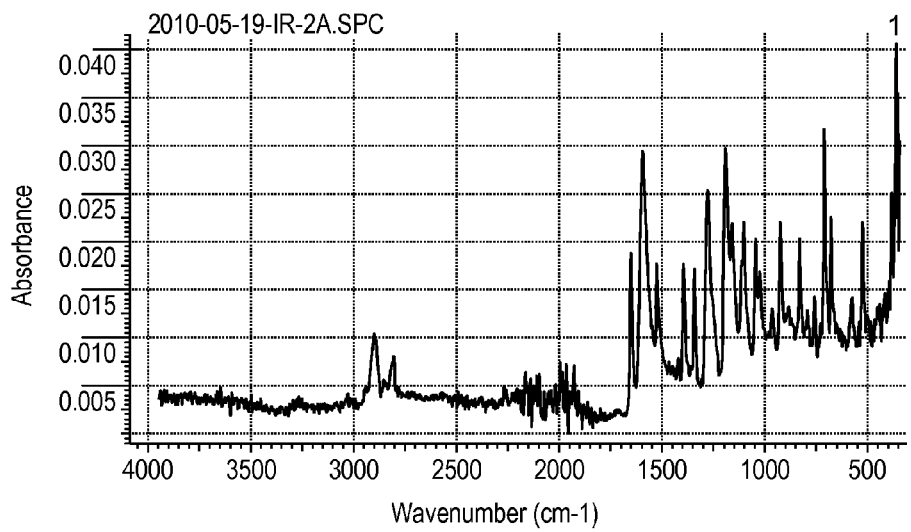
Figure 3:
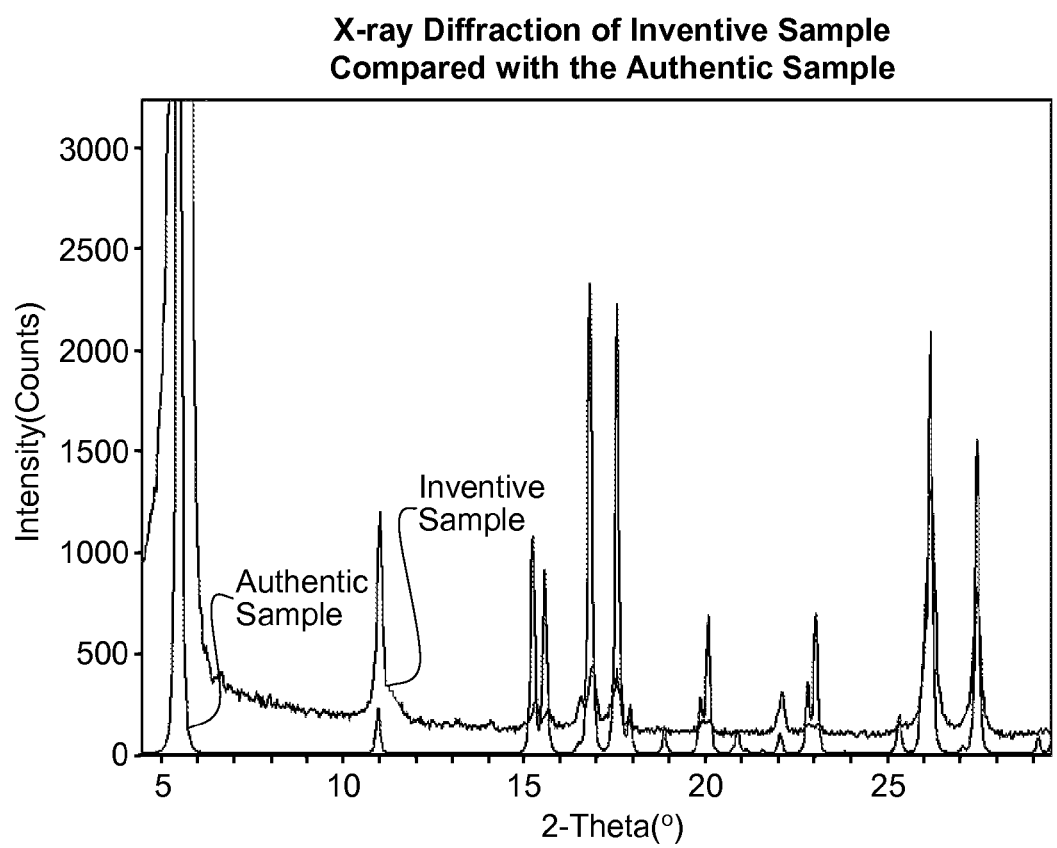

Conversion of di-(cyclopentylammonium)-4,8-bis(cyclopentylcarbamoyl)-naphthalene-1,5-dicarboxylate as a Mixture of trans and cis isomers (Compounds I-26 and I-29) to N,N'-bis-cyclopentyl Naphthalene Diimide in Solid State A solution of di-(cyclopentylammonium)-4,8-bis(cyclopentylcarbamoyl)-naphthalene-1,5-dicarboxylate salt in methanol (2 weight %) was spin coated on a glass plate and solvent evaporated at 40-50° C. The thin solid film of the salt was then heated at 180° C. for 10 minutes and resulting product dissolved in CDCl$_3$ and $^1$H NMR spectrum recorded and compared with an authentic sample of N,N'-bis(cyclopentyl)naphthalene diimide. The 1H NMR spectrum of the product obtained by solid state thermal conversion of amic acid salt was identical to that of the authentic sample. This clearly demonstrated that the amic acid salt can be easily converted to the corresponding diimide in thin solid film. $^1$H NMR (CDCl$_3$, 300 MHz) δ(ppm)=8.72 (s, 4H), 5.55 (q, 2H, J=8.2 Hz), 2.35-1.37 (m, 16H). IR spectra before and after heating clearly showed the formation of diimide in thin solid film (see FIGS. 2a and 2b). Furthermore the X-ray diffraction pattern of the N,N'-bis(cyclopentyl)naphthalene diimide prepared by solid state thermal conversion of precursor salt was identical to the powder X-ray diffraction pattern of the authentic sample (FIG. 3), confirming the high purity of diimide obtained by the described method.

OTFT Test Device Preparation Employing an Arylene Diimide Generated from an Amic Acid Salt:

Dielectric Preparation:

A heavily doped Si wafer with thermally grown SiO$_2$ (200 nm) dielectric layer was used as substrate. The SiO$_2$ surface was modified by spin-coating a 5 weight % solution of Cyclotene (3022-35, Dow) in mesitylene at 3000-5000 rpm. The Cyclotene-coated Si/SiO$_2$ wafer was placed on a hot plate and gradually heated from 50° C. to 150° C. under an inert atmosphere over a period of 15 minutes. Finally, the temperature was increased to 250° C. and was held for 30 minutes. Each sample was gradually cooled to room temperature over a period of 30 minutes. The thickness of each coated Cyclotene layer coated was in the range of 15 to 20 nm.

Coating of Salt Precursor and Thermal Conversion to Diimide:

A 0.5 weight % solution of di-(cyclopentylammonium)-4,8-bis(cyclopentylcarbamoyl)-naphthalene-1,5-dicarboxylate (as a mixture of trans- and cis-isomers of Compounds I-26 and I-29) in ethanol-CHCl$_3$ (1:1) containing triethylamine (2 weight %) was spin coated on Cyclotene modified SiO$_2$ surface. Sample was heated on a hotplate initially at 50° C. to remove the solvent and then temperature was raised to 180° C. over a period of about 5 minutes and the wafer was heated at 180° C. for 10 minutes in air. The resulting thin film of N,N'-bis(cyclopentyl)naphthalene diimide was used as a n-type semiconductor. The thickness of the semiconductor layer was a variable in some experiments, but was estimated to be 17-25 nm. OTFT devices using top source-drain contact configuration were made by depositing gold source drain contacts of thickness 60 nm through a shadow mask. The channel width was held at 650 μm while the channel lengths were varied between 50 and 150 μm.

Device Measurement and Analysis:

Electrical characterization of the devices prepared above was performed using a Hewlett Packard HP 4145B® semiconductor parameter analyzer. The probe measurement station was held in a positive argon environment for all measurements with the exception of those purposely used for testing the stability of the devices in air. For each experiment performed, between 4 and 12 individual devices were tested on each sample prepared, and the results were averaged. For each device, the drain current ($I_d$) was measured as a function of source-drain voltage ($V_d$) for various values of gate voltage ($V_g$). For most devices, $V_d$ was swept from 0 V to 100 V for each of the gate voltages measured, typically 0 V, 25 V, 75 V, and 100 V. In these measurements, the gate current ($I_g$) was also recorded in order to detect any leakage current through the device. Furthermore, for each device the drain current was measured as a function of gate voltage for various values of source-drain voltage. For most of the devices, Vg was swept from 0 V to 100 V for each of the drain voltages measured, typically 25 V, 75 V, and 100 V.

The log of the drain current as a function of gate voltage was plotted. Parameters extracted from the log $I_d$ plot included the $I_{on}/I_{off}$ ratio and the sub-threshold slope (S). The $I_{on}/I_{off}$ ratio is simply the ratio of the maximum to minimum drain current, and S is the inverse of the slope of the $I_d$ curve in the region over which the drain current is increasing (that is, when the device is turning on).

Figure 4A:
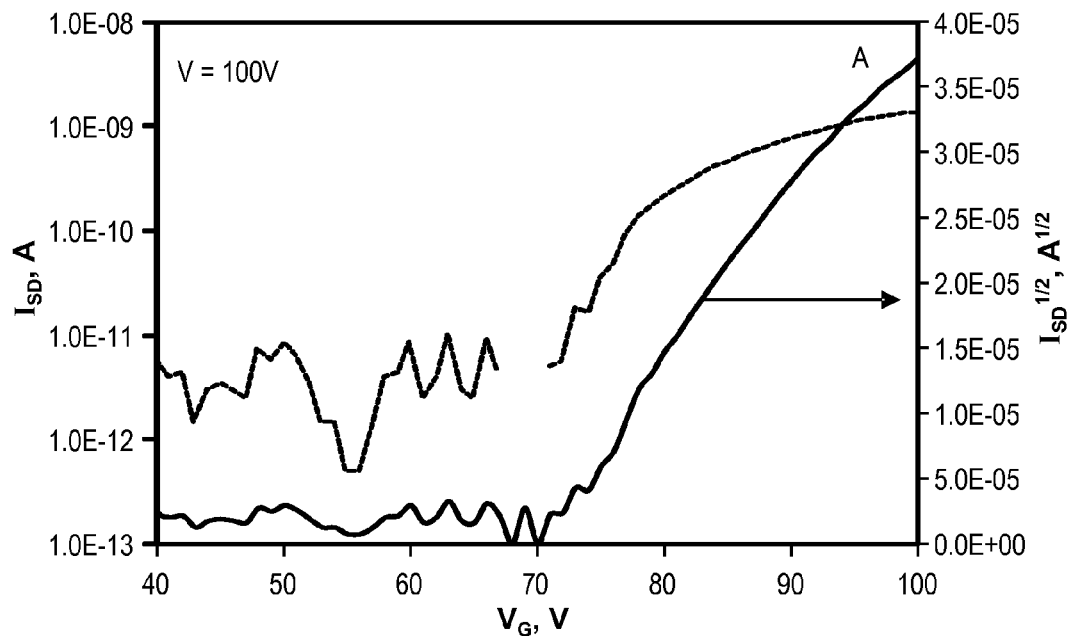
FIGS. 4a and 4b are graphical plots of performance data obtained for the devices described below in Invention Example 2.

The thin film transistor devices were evaluated in an argon atmosphere using a Hewlett-Packard 4145B® semiconductor parameter analyzer. For each thin film transistor device, the field effect mobility (μ) was calculated from the slope of the $(I_d)^{1/2}$ versus $V_g$ plot (FIG. 4a). This plot shows the square root of $I_d$ vs. $V_g$ and a mobility of 2×10$^{-5}$ cm$^2$/V.sec was calculated from this plot. The threshold voltage $V_T$=71 V and current modulation, as can be seen from FIG. 4a, between the on and the off state of the device was about 10$^3$.

Figure 4B:
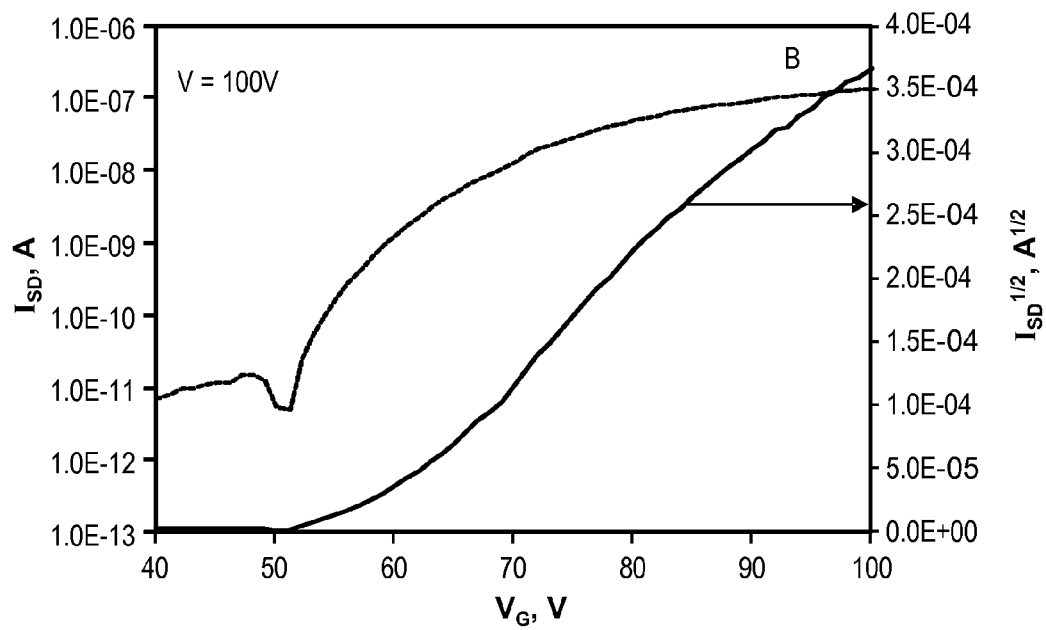

Device Comparison with Authentic Sample:

For comparison, a similar device was prepared using an authentic sample of the diimide. Accordingly, a 2 weight % solution of N,N'-bis(cyclopentyl)naphthalene diimide in chloroform was spin coated onto Cyclotene modified SiO$_2$ dielectric. Solvent was evaporated on a hot plate and top source-drain silver contacts of thickness 60 nm deposited through a shadow mask. The channel width was held at 650 μm while the channel lengths were varied between 50 and 150 μm. The field effect mobility (μ) calculated from the slope of the $(I_d)^{1/2}$ versus $V_g$ plot (FIG. 4b) was of 1×10$^{-4}$ cm$^2$/V.sec was calculated from this plot. The threshold voltage $V_T$=67 V and current modulation, as can be seen from FIG. 4b, between the on and the off state of the device was about 10$^4$.

This example clearly demonstrates that the semiconductive performance of an arylene diimide obtained via thin solid film thermal conversion of an aromatic, non-polymeric amic acid salt performed comparable to an authentic arylene diimide.

Invention Example 3

Preparation of di-(cyclohexylammonium)-4,8-bis(cyclohexylcarbamoyl)-naphthalene-1,5-dicarboxylate as a Mixture of trans and cis isomers

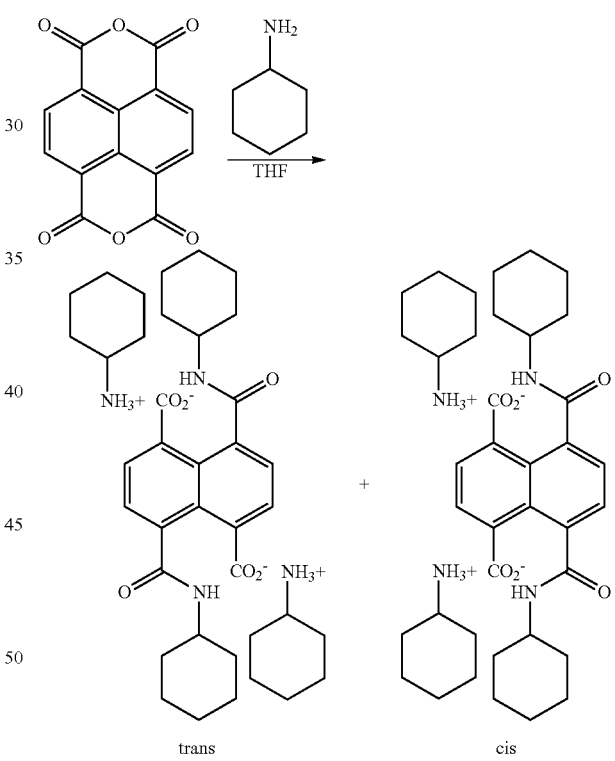

trans          cis

To a stirred dispersion of 1,4,5,8-naphthalene tetracarboxylic acid dianhydride (46 mg, 0.17 mmol) in tetrahydrofuran (4 ml), a solution of cyclohexylamine (68 mg, 0.68 mmol) in tetrahydrofuran (1 ml) was added dropwise to obtain first a clear pale yellow solution that quickly turned cloudy. Stirring was continued for an additional 5 minutes, then excess diethyl ether was added to obtain a precipitate that was filtered, washed with diethyl ether, and dried in air.

$^1$H and $^{13}$C NMR spectra of the product were consistent with the salt being a mixture of cis and trans isomers. The aromatic protons of the trans-isomer appeared as a two doublets at 7.78 ppm (J=7.60 Hz) and 7.63 ppm (J~7 Hz); aromatic protons of the cis isomer appeared as singlets at 7.81 ppm and 7.61 ppm. From the integrated areas of the aromatic protons, it was determined that the product was a 1:1 mixture of cis and trans amic acid salt. $^1$H NMR (CD$_3$OD, 300 MHz) δ(ppm)=7.81 ppm (s, 2H, cis isomer), 7.78 (2H, J=7.60 Hz, trans isomer), 7.63 (s, 2H, J=7 Hz, trans isomer), 7.61 (s, 2H, cis isomer), 3.90-3.78 (m, 2H), 3.0-2.86 (m, 2H), 2.09-2.16 (m, 4H), 1.98-1.60 (m, 18H), 1.5-1.1 (m, 20H). $^{13}$C NMR (CD$_3$OD) δ(ppm)=175.23, 170.46, 141.38, 140.01, 137.94, 136.63, 128.46, 128.43, 127.09, 126.78, 126.23, 125.97, 51.15, 49.29, 49.25, 32.47, 31.04, 25.70, 25.20, 24.81.

The invention has been described in detail with particular reference to certain preferred embodiments thereof, but it will be understood that variations and modifications can be effected within the spirit and scope of the invention.

PARTS LIST 10 substrate
20 gate dielectric
30 semiconductor
40 source electrode
50 drain electrode
60 gate electrode

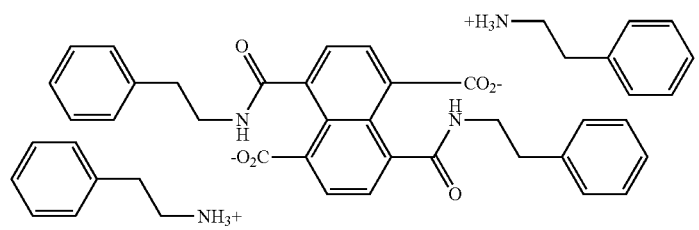

I-5
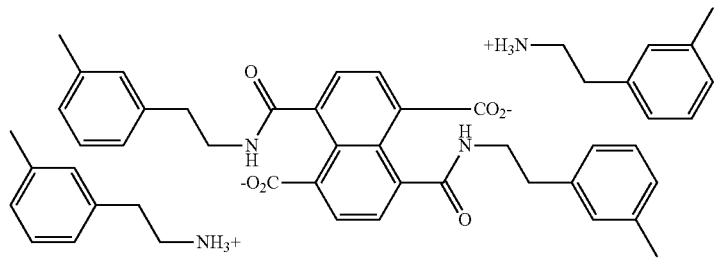
I-8
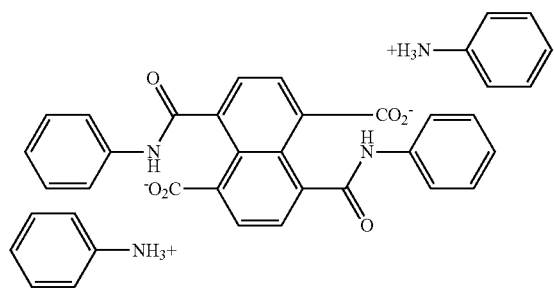
I-9
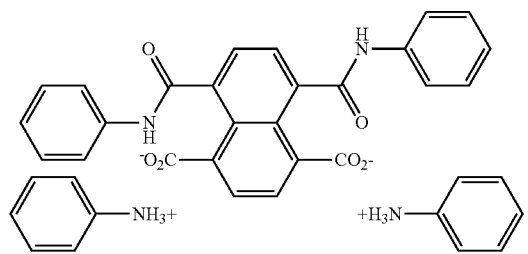
I-10
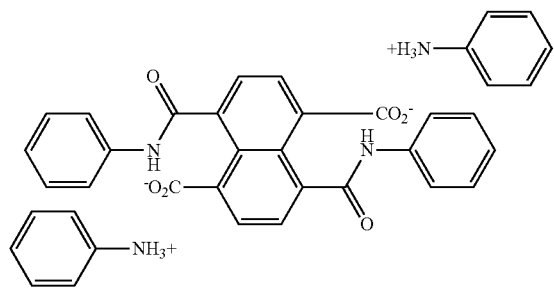
I-13
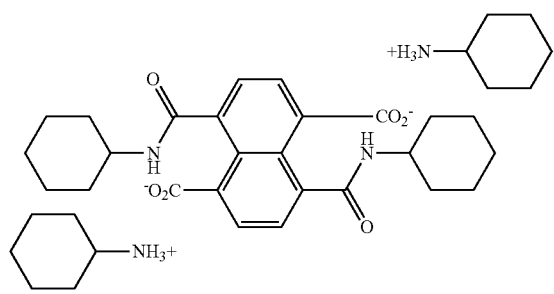

-continued
I-16
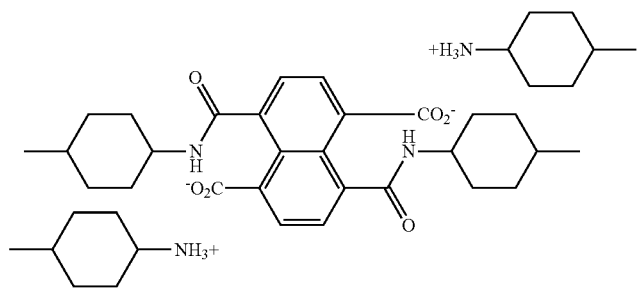
I-19
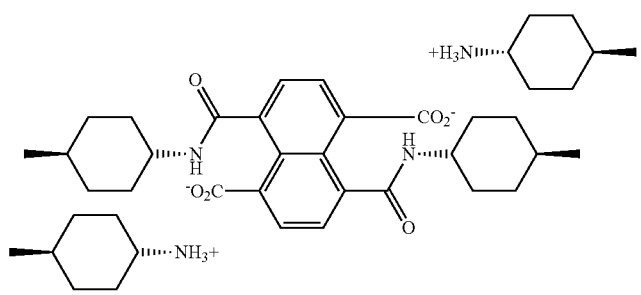
I-20
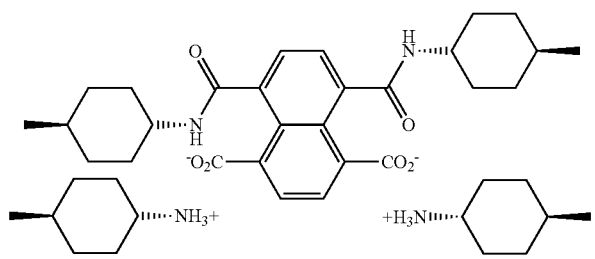
I-21
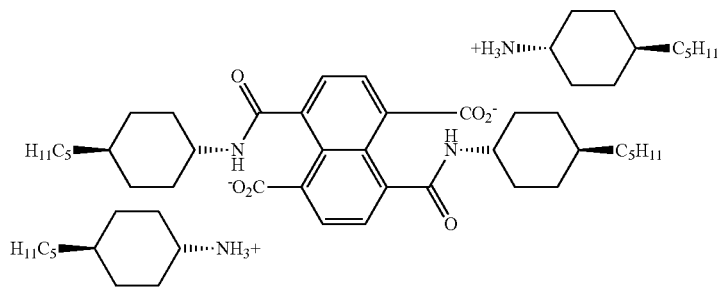
I-22
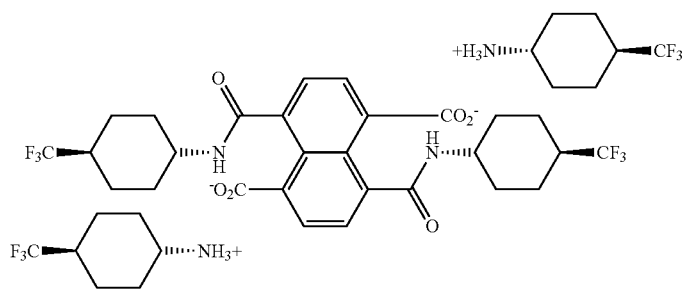

I-24
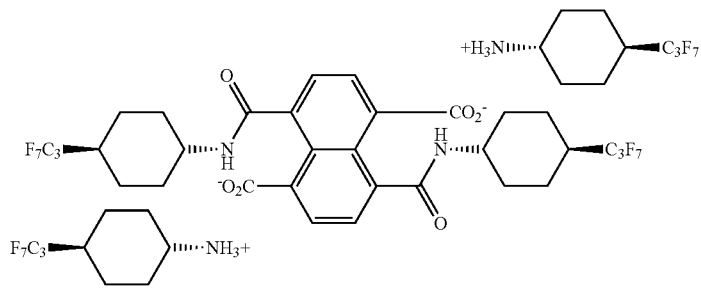
I-25
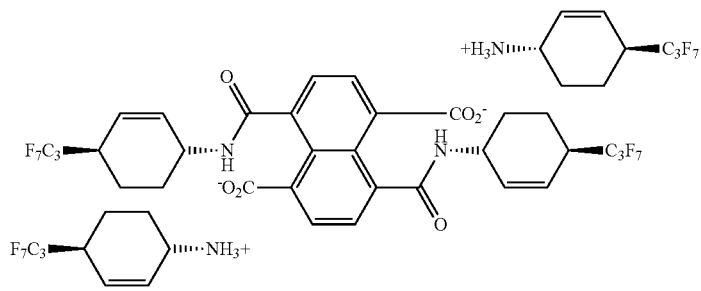
I-26
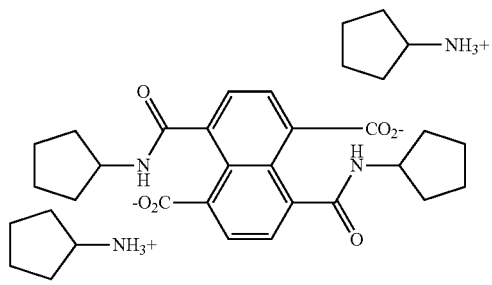
I-29
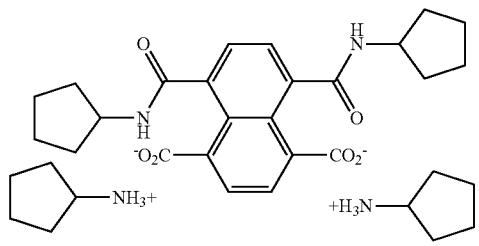
I-36
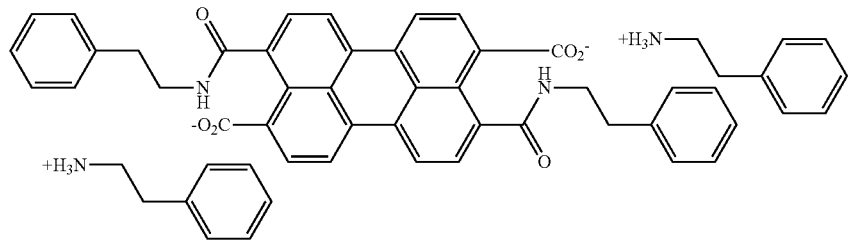

-continued
I-37
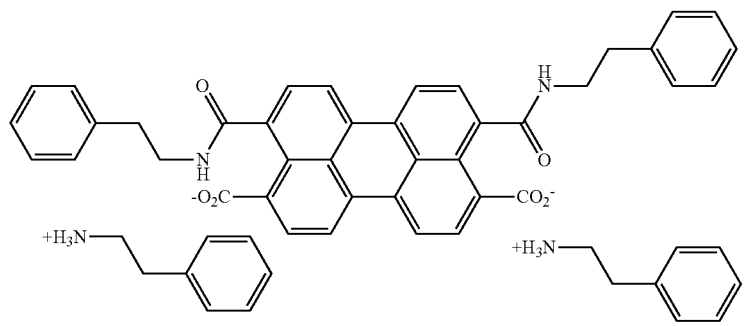
I-39
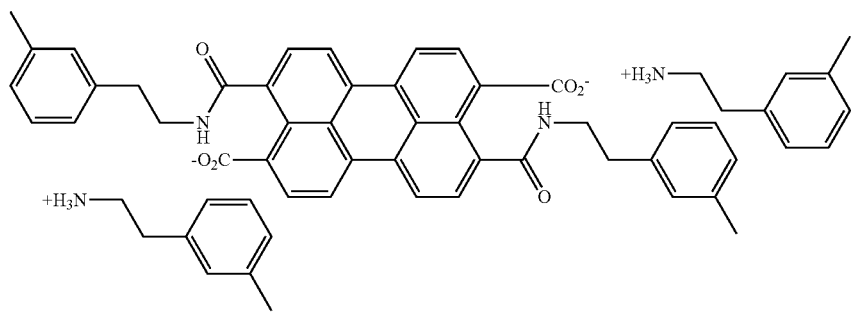
I-41
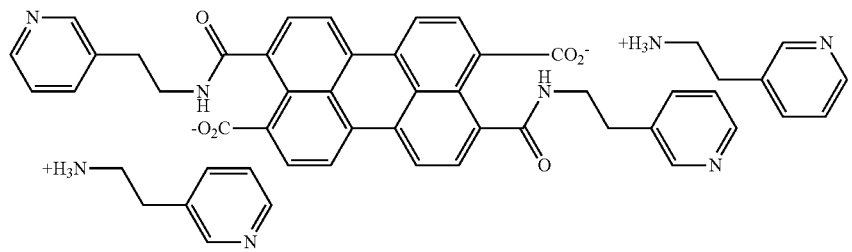
I-42
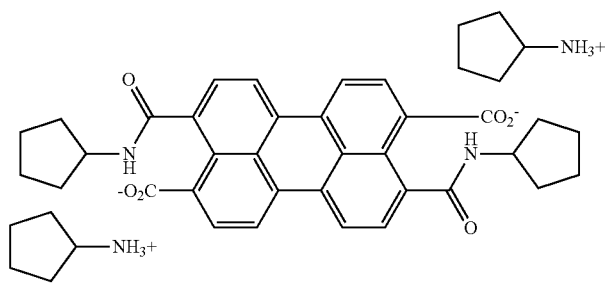
I-44
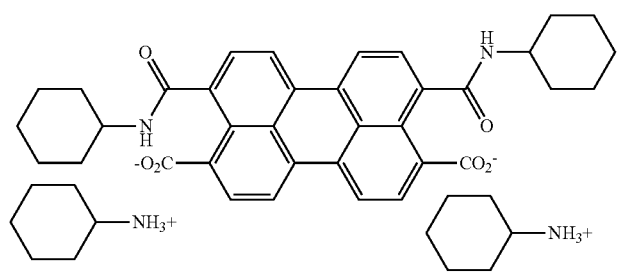

I-45 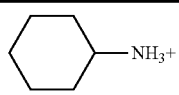
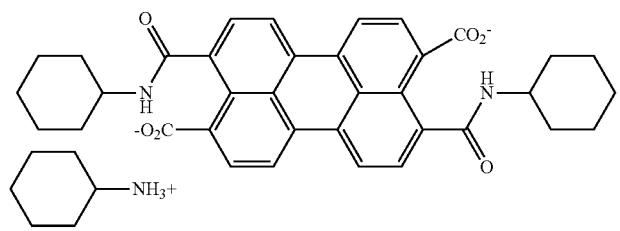
I-49 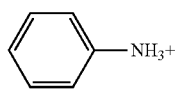
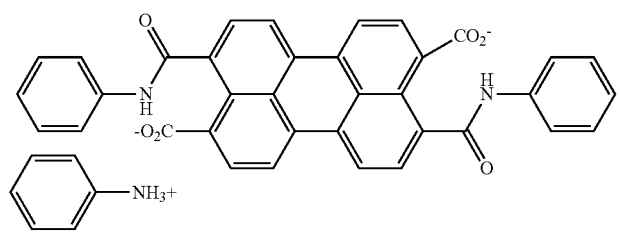
I-50
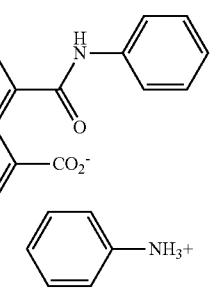
I-51 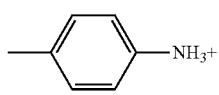
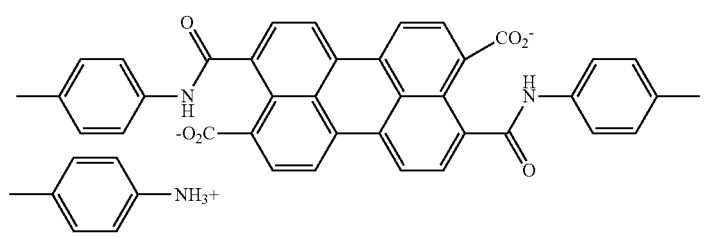
I-52 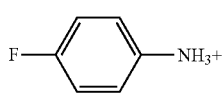
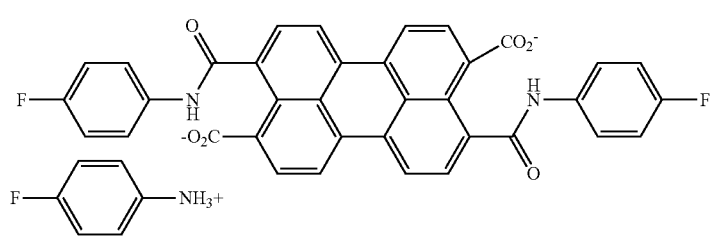

I-53
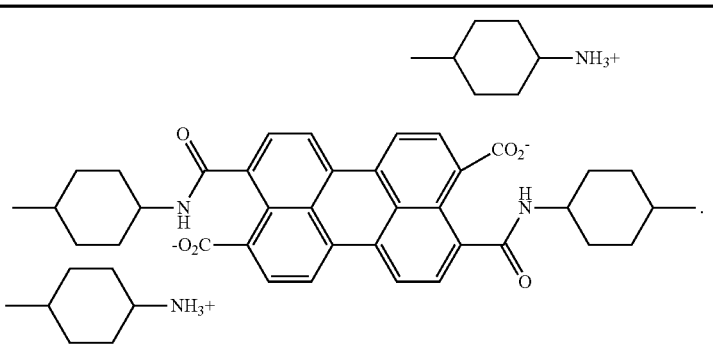

The invention claimed is:

1. An organic composition that comprises an aromatic, non-polymeric amic acid salt,
wherein the aromatic, non-polymeric amic acid salt is represented by the following Structure (I):

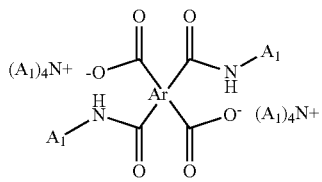
(I)

wherein: Ar is a naphthalene or perylene nucleus and the four carbonyl groups are attached directly to peri carbon atoms, the non-cation A$_1$ group is a aryl, heteroaryl, non-aromatic alkyl, alkylaryl, fluoroalkyl, cycloalkyl, or heterocyclyl group, and the four A$_1$ groups in the cation are hydrogen atoms.

2. The composition of claim 1 including one or more organic solvents in which the aromatic, non-polymeric amic acid salt is soluble or dispersible.

3. The composition of claim 2 wherein the aromatic, non-polymeric amic acid salt is present in an amount of at least 0.5 and up to and including 50 weight % based on total composition weight.

4. The composition of claim 1 that consists essentially of the aromatic, non-polymeric amic acid salt and an amine catalyst.

5. An organic composition that comprises an aromatic, non-polymeric amic acid salt that is represented by the following Structure (I):

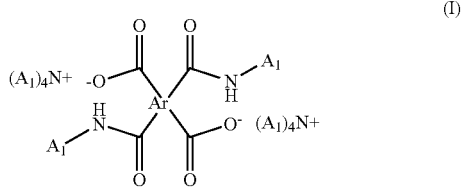
(I)

wherein Ar is an anthracene, naphthalene, or perylene nucleus and the four carbonyl groups are attached directly to peri carbon atoms, the non-cation A$_1$, A$_2$, and A$_3$ groups are independently aryl, heteroaryl, non-aromatic alkyl, alkylaryl, fluoroalkyl, cycloalkyl, or heterocyclyl groups, and two, three, or four A$_1$ groups in the cations represent the same or different non-aromatic alkyl, and any remaining A$_1$ groups in the cations are hydrogen atoms.

6. The organic composition of claim 5 wherein the aromatic, non-polymeric amic acid salt is one or more of the following compounds:

I-3
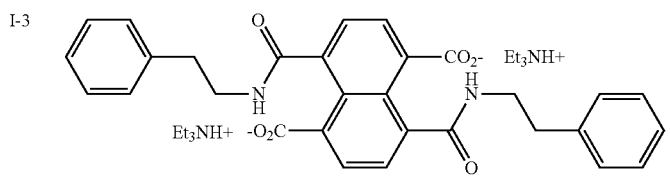

I-4
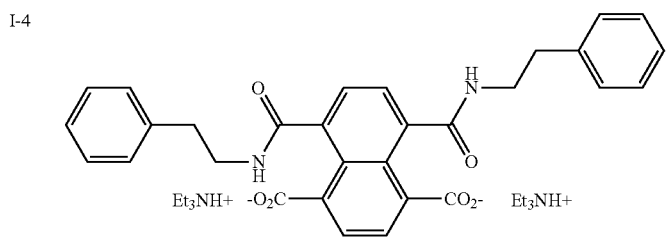

-continued
I-6
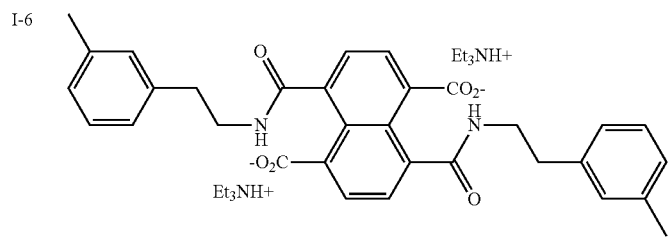
I-7
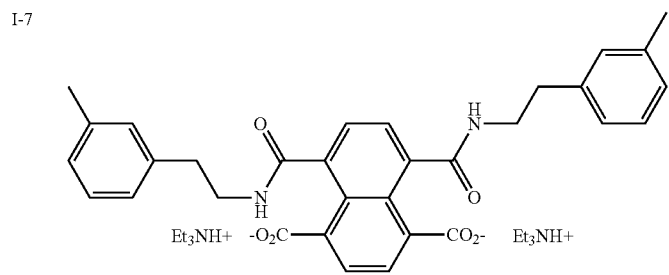
I-11
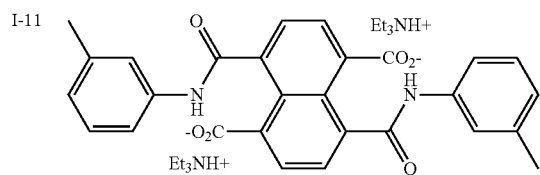
I-12
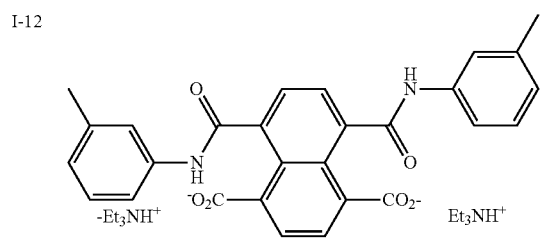
I-14
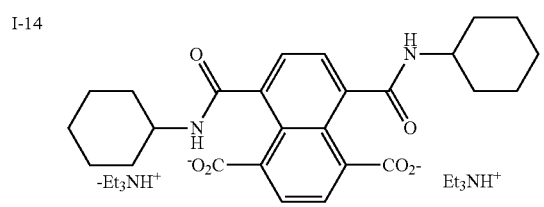
I-15
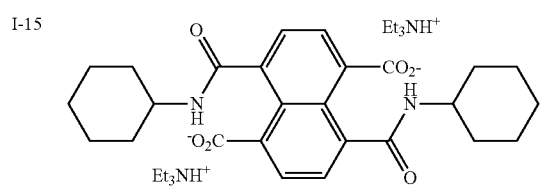
I-17
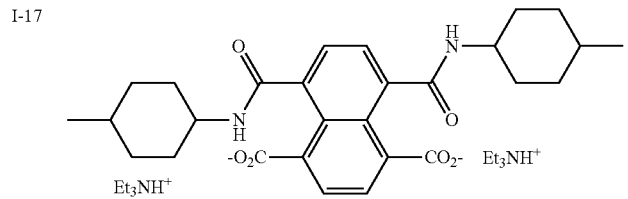

-continued
I-18
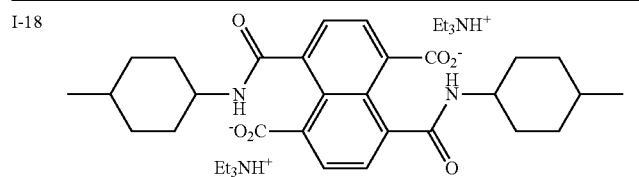
I-23
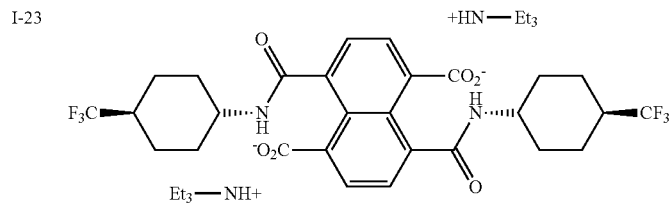
I-27
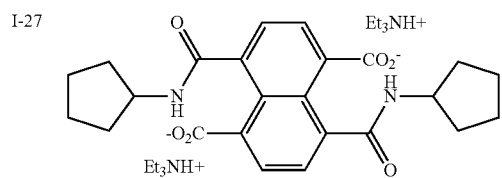
I-28
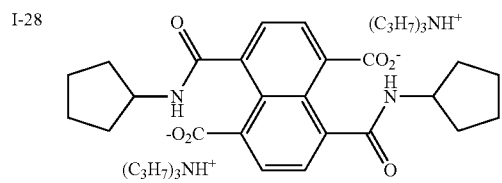
I-30
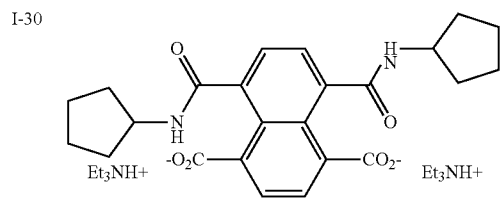
I-33
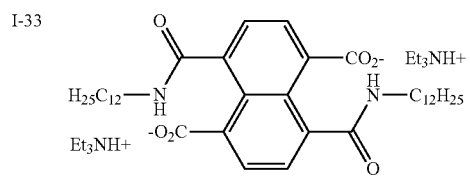
I-35
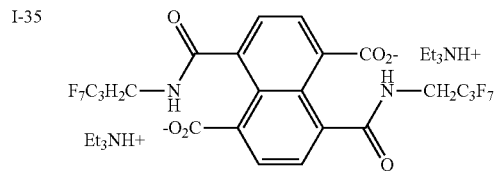
I-38
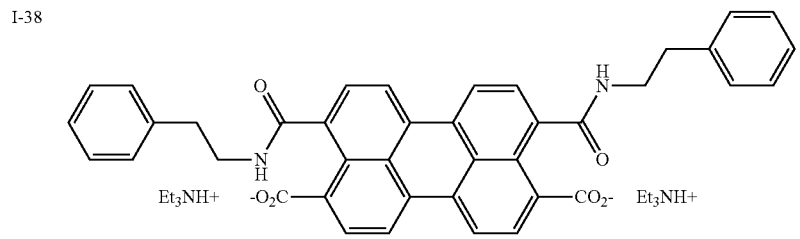

I-40

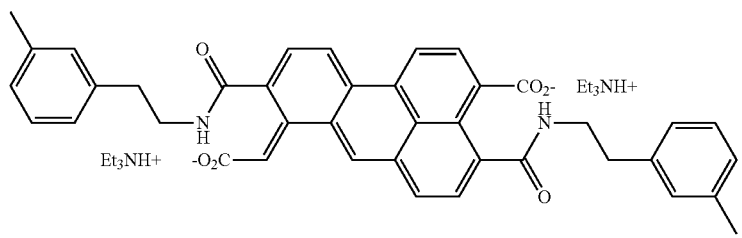

I-43

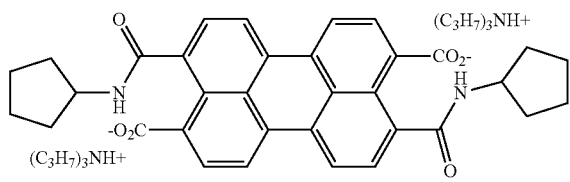

I-48

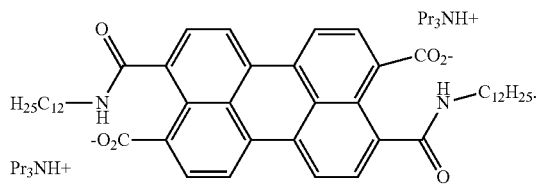

7. An organic composition that comprises an aromatic, non-polymeric amic acid salt that is represented by the following Structure (I):

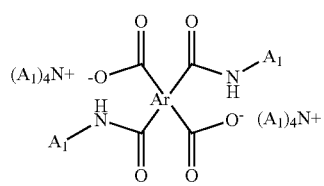

(I)

wherein Ar is an anthracene, naphthalene, or perylene nucleus and the four carbonyl groups are attached directly to peri carbon atoms, the non-cation $A_1$, $A_2$, and $A_3$ groups are independently aryl, heteroaryl, non-aromatic alkyl, alkylaryl, fluoroalkyl, cycloalkyl, or heterocyclyl groups, and at least one $A_1$ group in the cations is a aryl, heteroaryl, alkylaryl, fluoroalkyl, cycloalkyl, or heterocyclyl group, and the rest of the $A_1$ groups in the cations are hydrogen atoms.

8. The composition of claim 7 wherein the aromatic, non-polymeric amic acid salt is one or more of the following compounds:

I-1

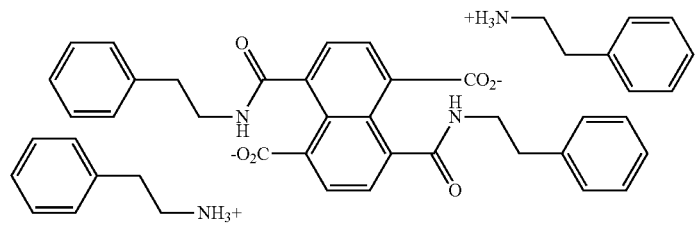

I-2